(12) United States Patent
Hua et al.

(10) Patent No.: US 6,916,824 B1
(45) Date of Patent: Jul. 12, 2005

(54) METHODS OF TREATING CATARACTS AND DIABETIC RETINOPATHY WITH TRICYCLIC PYRONES

(75) Inventors: Duy H. Hua, Manhattan, KS (US); Dolores J. Takemoto, Manhattan, KS (US); Alan Brightman, Manhattan, KS (US); Bradley W. Fenwick, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 09/712,612

(22) Filed: Nov. 13, 2000

Related U.S. Application Data

(60) Provisional application No. 60/165,151, filed on Nov. 12, 1999.

(51) Int. Cl.[7] .............................................. A61K 31/44
(52) U.S. Cl. ........................ 514/291; 514/292; 514/912
(58) Field of Search ................................. 514/291, 292, 514/912

(56) References Cited

U.S. PATENT DOCUMENTS 5,958,970 A    9/1999  Hua et al. ................... 514/455

OTHER PUBLICATIONS

Aiello et al., (Mar. 1999), "Amelioration of Abnormal Retinal Memodynamics by a Protein Kinase C β–Selective Inhibitor (LY33531) in Patients with Diabetes: Results of a Phase I Safety and Pharmacodynamic Clinical Trial," *IVOS* 40:S192.

Cervera et al., (1990), "4–Amino–6–Methyl–2H–Pyran–2–One. Preparation and Reactions with Aromatic Aldehydes," *Tetrahedron* 46:7885–7892.

Dess, D.B. and Martin, J.C. (1983), "Readily accessible 12–I–5[1] Oxidant for the Conversion of Primary and Secondary Alcohols to Aldehydes and Ketones," *J. Org. Chem.* 48:4155–4156.

Hua et al., (1997), "(5aS,7S)–7–Isopropenyl–3—methyl–5a,6,8,9–tetrahedro–1H,7H–pyrano[4,3–b][1] benzopyran–1–one," *Acta Cryst* C53:1995–1997.

Hua et al., (1997), A One–Pot Condensation of Pyrones and Enals. Synthesis of 1H,7H–5a,6,8,9–Tetrahydro–1–oxopyrano[4,3–b]benzopyrans. *J. Org. Chem.* 62:6888–6896.

Urzhumtsev et al., (1997), "A 'specificity' pocket inferred from the crystal structures of the complexes of aldose reductase with the pharmaceutically important inhibitors tolrestat and sorbinil," *Structure* 5:601–612.

Vedejs et al., (1978), "Transition–Metal Peroxide Reaction. Synthesis of α–Hydroxycarbonyl Compounds from Enolates," *J. Org. Chem.* 43:188–196.

Williamson et al., (Mar. 1999), "Ocular and Cerebral Vascular Dysfunction Induced by Diabetes and by LY33531, a β–Selective Inhibitor of Protein Kinase C," *IOVS* 40:S369.

*Primary Examiner*—Zohreh Fay
(74) *Attorney, Agent, or Firm*—Greenlee, Winner and Sullivan, P.C.

(57) ABSTRACT

Water-soluble, cell permeable aldose reductase inhibitors are presented. These compounds prevent the effects of galactosemia in patients. The compounds prevent both the accumulation of polyols and the change in levels of protein kinase C gamma observed during diabetes and galactosemia.

8 Claims, 4 Drawing Sheets

Lens

Sciatic Nerves

METHODS OF TREATING CATARACTS AND DIABETIC RETINOPATHY WITH TRICYCLIC PYRONES

CROSS-REFERENCE TO RELATED APPLICATIONS

This application claims priority to U.S. Provisional Patent application Ser. No. 60/165,151, filed Nov. 12, 1999, which is hereby incorporated by reference to the extent not inconsistent with the disclosure herein.

BACKGROUND OF THE INVENTION

Diabetes has many long term complications, including nephropathy, neuropathy and retinopathy. Retinopathy is primarily a vascular disease brought on by high glucose and resulting damage to vascular tissue with subsequent damage to retinal tissues. Aldose reductase catalyzes the reduction of aldehyde sugars to their alcohol forms; D-glucose is reduced to sorbitol and galactose to galactitol. Under normal conditions the sorbitol pathway plays a minor role in glucose metabolism. However, in hyperglycemia associated with diabetic cells, which have high aldose reductase, glucose and sorbitol levels increase. Due to poor transport out of the cells, the sorbitol accumulates and causes osmotic damage to cells. The lens, retina and peripheral nerves are particularly affected. This has led to the development of drugs, which inhibit aldose reductase activity. Although aldose reductase inhibitors (ARI's) have been used to treat nephropathy and neuropathy, there is no known pharmaceutical treatment for retinopathy. The ineffectiveness of ARI's in treating retinopathy may arise from the insolubility of the drugs in water and the short lifetime (about one half hour in the human body) of these drugs. Current treatment options for retinopathy include surgery and better control of blood glucose, neither of which is completely successful in preventing blindness.

TABLE 1

Known ARI's

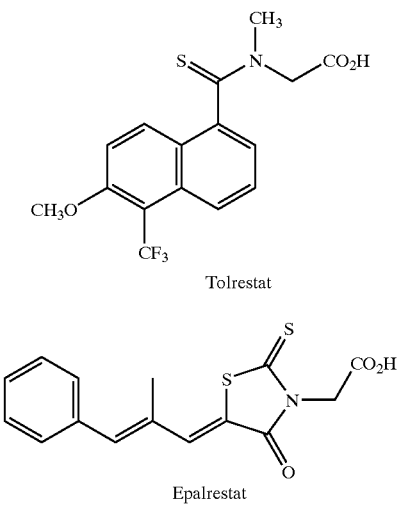

Tolrestat

Epalrestat

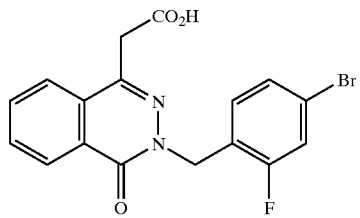

Ponalrestat (Statil)

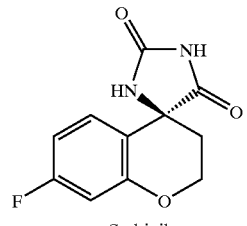

Sorbinil

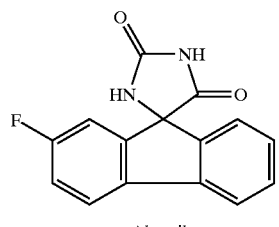

Alconil

In addition to the osmotic damage from sorbitol accumulation, the additional flux of glucose through metabolic pathways leads to increased production of diacylglycerol. This leads to cellular changes in the enzyme protein kinase C (PKC). There are various forms of PKC. The PKCβ isoform is abundant in vascular tissue where it plays a role in the maintenance of the normal growth of vascular endothelial cells and pericytes. On the other hand, this isoform is not found in vascular tissue such as lens. In lens and peripheral nerves, a major isoform is PKCγ, an isoform which decreases during diabetes and which functions to control gap junction communication.

Currently, there are five active ARI's reported: Tolrestat, Epalrestat, Ponalrestat, Sorbinil, and Alconil (Table 1). Tolrestat is currently marketed for neuropathy in humans. Currently there are no drugs available for use in dogs.

Because protein kinase C level in diabetes is abnormally high, selective inhibition of protein kinase C-β (PKC-β) has been studied in animals and found to result in normalized retinal blood flow. However, Phase I trials of the drugs used indicate that they may have undesirable side effects. (Aiello, L. et al. Amelioration of Abnormal Retinal Memodynamics by a Protein Kinase C β-Selective Inhibitor (LY33531) in Patients with Diabetes: Results of a Phase I Safety and Pharmacodynanic Clinical Trial. *IOVS.* 1999, 40, S192; Williamson, J. et al. Ocular and Cerebral Vascular Dysfunction Induced by Diabetes and by LY33531, a β-Selective Inhibitor of Protein Kinase C. *IOVS.* 1999, 40, S369).

There is a need for drugs that are cell permeable, water soluble and more effective than currently available treatments for the complications of diabetes.

SUMMARY OF THE INVENTION

This invention provides tricyclic compounds having hydrocarbyl substituents which are useful in treating the complications of diabetes.

Preferably, the invention provides tricyclic compounds of the formula:

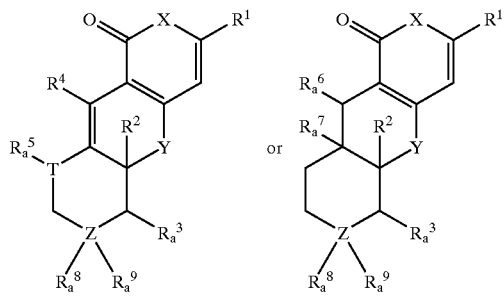

wherein:

T is independently CR, NR, N, S or O;
X is independently O, NR, N or S;
Y is independently O, NR, N or S;
Z is independently C, N, S or O;
a is 0 or 1,
$R^1$, $R^3$, $R^4$ and $R^5$ are, independently, R,

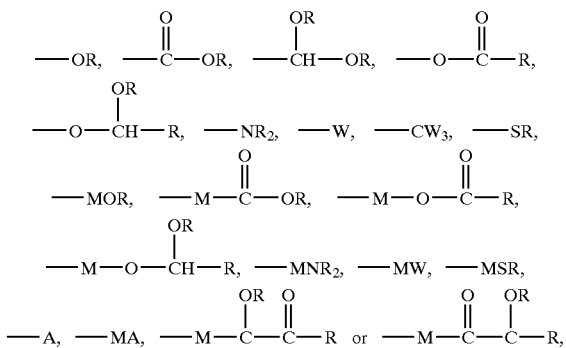

wherein R is independently H, OH, alkyl, alkenyl or alkynyl, an aromatic ring system, amino, sulfhydryl, or sulfonyl, M is a divalent alkyl, alkenyl or alkynyl, aromatic ring system, or sulfonyl, W is Cl, F, Br or OCl, and A is an aromatic ring system;
$R^2$, $R^8$ and $R^9$ are independently R as defined above; and
$R^6$ is independently R, $NH_2$, OH, or OCOR where R is as set forth above;
$R^7$ is independently OH or H; or
$R^6$ and $R^7$ taken together are O;

and pharmaceutically acceptable salts or esters of the foregoing, as well as optical isomers thereof.

Provided are methods of treating a symptom or condition that results from the activity of aldose reductase comprising administering to a patient an effective amount of one or more compounds of the formula:

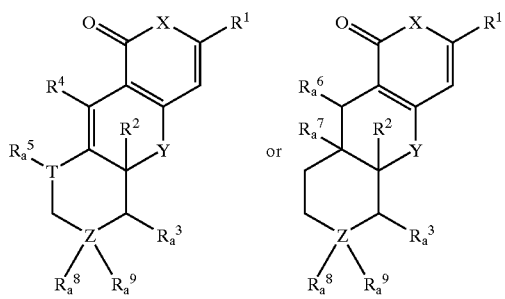

wherein:

T is independently CR, NR, N, S or O;
X is independently O, NR, N or S;
Y is independently O, NR, N or S;
Z is independently C, N, S or O;
a is 0 or 1,
$R^1$, $R^3$, $R^4$ and $R^5$ are, independently, R,

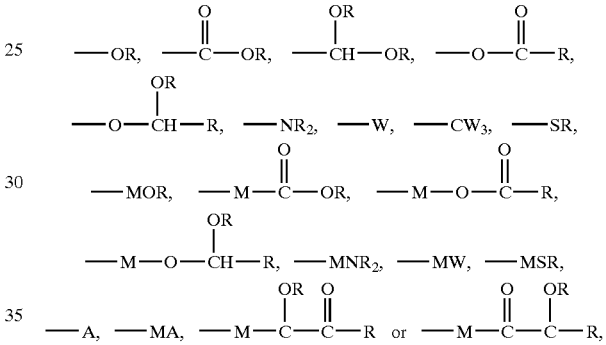

wherein R is independently H, OH, alkyl, alkenyl or alkynyl, an aromatic ring system, amino, sulfhydryl, or sulfonyl, M is a divalent alkyl, alkenyl or alkynyl, aromatic ring system, or sulfonyl, W is Cl, F, Br or OCl, and A is an aromatic ring system;
$R^2$, $R^8$ and $R^9$ are independently R as defined above; and
$R^6$ is independently R, $NH_2$, OH, or OCOR where R is as set forth above;
$R^7$ is independently OH or H; or
$R^6$ and $R^7$ taken together are O;

and pharmaceutically acceptable salts or esters of the foregoing, as well as optical isomers thereof. Preferably, the patient is a dog or human and the compound is compound 1. Also provided are methods of inhibiting aldose reductase activity in cells, comprising contacting the cells with an effective amount of a compound of the invention. Also provided is a method for treating retinopathy comprising administering to a patient an effective amount of a compound of the invention. Also provided is a method for decreasing the loss of PKC in diabetic patients or inhibiting polyol accumulation in diabetic patients comprising administering to a patient an effective amount of a compound of the invention. Pharmaceutical compositions comprising a compound of the invention wherein the composition is useful to treat a disorder associated with the activity of aldose reductase are provided. A method of preparing a pharmaceutical composition comprising bringing a compound of formula

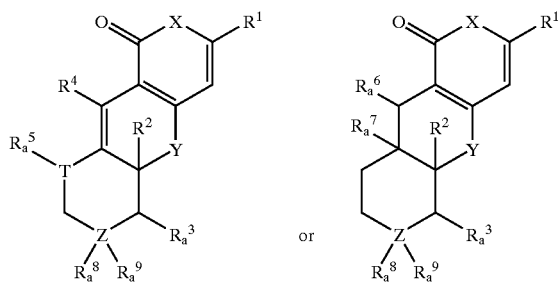

wherein:
T is independently CR, NR, N, S or O;
X is independently O, NR, N or S;
Y is independently O, NR, N or S;
Z is independently C, N, S or O;
a is 0 or 1,
$R^1$, $R^3$, $R^4$ and $R^5$ are, independently, R,

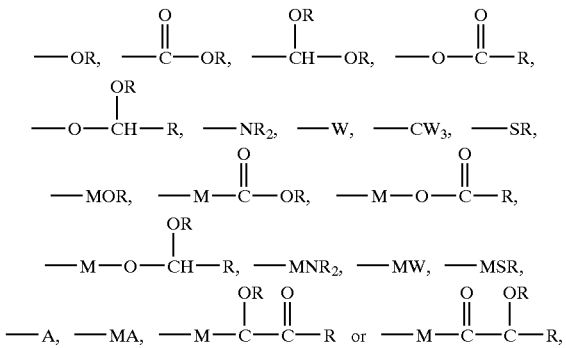

wherein R is independently H, OH, alkyl, alkenyl or alkynyl, an aromatic ring system, amino, sulfhydryl, or sulfonyl, M is a divalent alkyl, alkenyl or alkynyl, aromatic ring system, or sulfonyl, W is Cl, F, Br or OCl, and A is an aromatic ring system;
$R^2$, $R^8$ and $R^9$ are independently R as defined above; and
$R^6$ is independently R, $NH_2$, OH, or OCOR where R is as set forth above;
$R^7$ is independently OH or H; or
$R^6$ and $R^7$ taken together are O;
and pharmaceutically acceptable salts or esters of the foregoing, as well as optical isomers thereof into association with a pharmaceutically acceptable carrier are provided. Compounds not disclosed in U.S. Pat. No. 5,958,970 and U.S. Ser. No. 09/338,999 are also provided, including

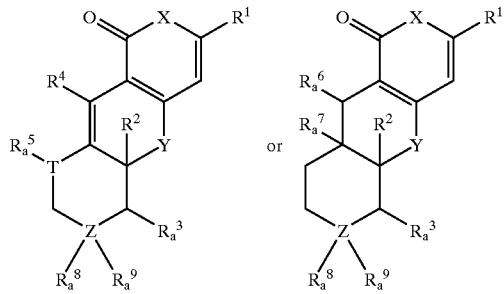

wherein:
T is independently CR, NR, N, S or O;
X is independently O, NR, N or S;
Y is independently O, NR, N or S;
Z is independently C, N, S or O; a is 0 or 1,
$R^1$, $R^3$, $R^4$ and $R^5$ are, independently, R,

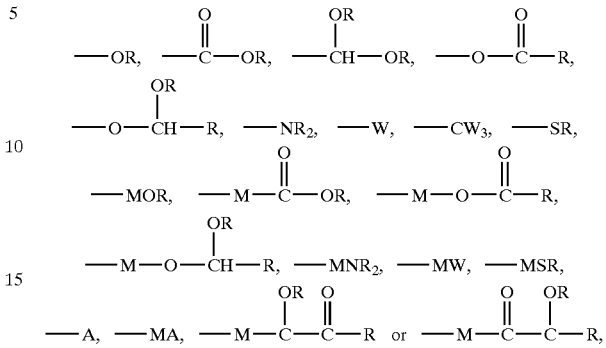

wherein R is independently H, OH, alkyl, alkenyl or alkynyl, an aromatic ring system, amino, sulfhydryl, or sulfonyl, M is a divalent alkyl, alkenyl or alkynyl, aromatic ring system, or sulfonyl, W is Cl, F, Br or OCl, and A is an aromatic ring system;
$R^2$, $R^8$ and $R^9$ are independently R as defined above; and
$R^6$ is independently R, $NH_2$, OH, or OCOR where R is as set forth above;
$R^7$ is independently OH or H; or
$R^6$ and $R^7$ taken together are O;
provided that either:
T is independently CR, provided that R is not H, or NR;
X is independently NR or N, provided that R is not H;
Y is independently NR, provided that R is not H; or
$R^1$, $R^3$, $R^4$ and $R^5$ are, independently,
—CH(OR)—OR; —O—CH(OR)—R; -M-O—CH(OR)—R; -M-C(OR)—C(=O)—R; or -M-C(=O)—C(OR)OR.

TABLE 2

Representative compounds

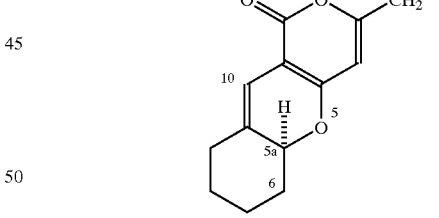

1: $IC_{50}$ = 2 nM

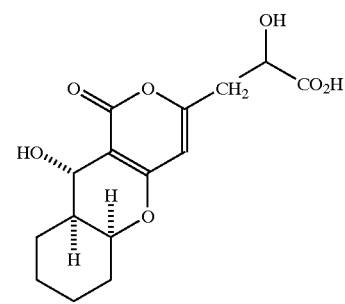

2: $IC_{50}$ = 20 nM

TABLE 2-continued
Representative compounds
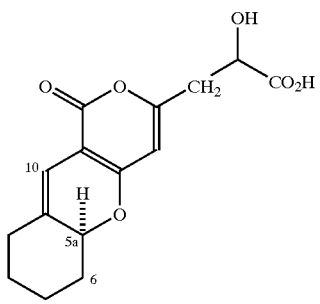
3: IC$_{50}$ = 100 nM
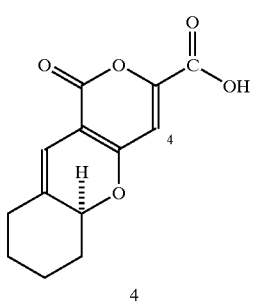
4
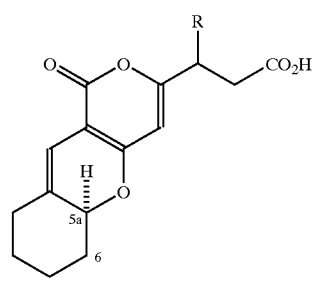
5a: R = H
5b: R = OH
5c: R = NH$_2$
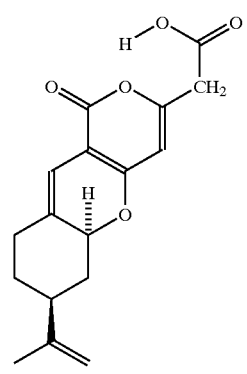
6
TABLE 2-continued
Representative compounds
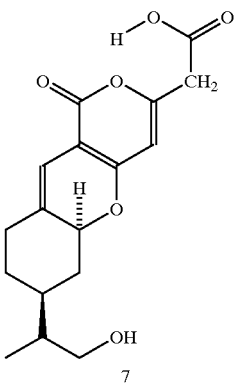
7
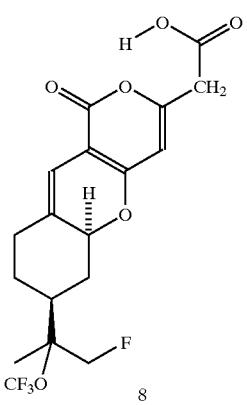
8
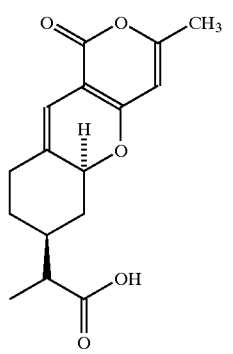
9
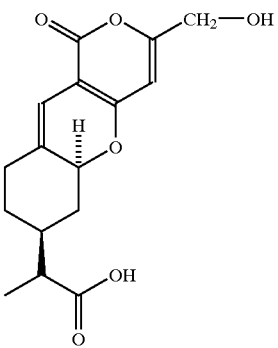
10

TABLE 2-continued

Representative compounds

11: R = H
12: R = —CMe=CH₂

13: R = H
14: R = —CMe=CH₂

Preferred compounds are those specifically depicted and described in this disclosure. A class of compounds of this invention includes Compounds 2, 3, 6, 7, 8, 9, 10, 11, 12, 13 and 14. A further class of compounds of this invention includes homologs of the foregoing compounds. A preferred class of compounds includes those where T and Z are C and X and Y are O. A preferred class of compounds includes those where $R^1$ is $CH_2CO_2H$. A preferred class of compounds includes those where Z is C and $R^8$ and $R^9$ are H. A class of compounds of this invention are those that inhibit aldose reductase to the same or greater extent than currently available aldose reductase inhibitors, including Tolrestat. A class of compounds of the invention are those that are water soluble.

The methods of the invention are useful in treating the diseases and disorders described herein in patients. Patients include small mammals, humans, large mammals, livestock animals, pets and laboratory animals. Preferably, the patient is a human or dog.

This invention also provides methods for inhibiting aldose reductase in cells, particularly lens epithelial cells, comprising contacting the cells with a tricyclic compound as disclosed herein, preferably in cell-permeable, water-soluble form. Methods are also provided for reducing the effects of high glucose and protein kinase C in tissues via administration of such compounds. This invention provides such compounds in suitable pharmaceutical carriers in dosages effective to provide measurable therapeutic results in inhibiting aldose reductase and ameliorating symptoms of cataract and/or diabetic retinopathy. Preferably, the compounds used in the methods of this invention are at least as effective or more effective inhibitors of human retina aldose reductase than Tolrestat, Sorbinil or other known aldose reductase inhibitors. One or more compounds of the invention may be used in combination.

Certain compounds of this invention were disclosed in U.S. Pat. No. 5,958,970 and U.S. Ser. No. 09/338,999, incorporated herein by reference to the extent not inconsistent herewith, and specifically for their disclosures of methods of preparing the subject compounds and for analogs of the compounds disclosed herein having substituents as defined herein. Methods of using such compounds as aldose reductase inhibitors are provided herein.

Compounds of this invention may be prepared and used without undue experimentation by those skilled in the art of synthetic chemistry by methods analogous to those specifically disclosed herein or in publications and patent applications incorporated by reference. Methods of selecting those compounds which are effective for inhibiting aldose reductase in cells to a desired level are performed without undue experimentation by those skilled in the art by the methods described herein, or those methods known in the art.

Compounds containing any combination of substituents or members of the Markush groups specified above are within the scope of the invention. All substituents of the compounds of the invention may be the same, all substituents may be different, or any combination of substituents may be the same or different. Compounds having substituents with a specified function, for example those that impart water solubility to the compound form a special class of compounds of this invention.

The substituents included in the compounds and used in the methods of the invention may be any substituent not having structures or reactivity which would substantially interfere with the desired aldose reductase inhibition of the compound, as may readily be determined without undue experimentation by those skilled in the art, for example, by using the assay methods disclosed herein. Preferably the substituents do not interfere with water-solubility of the compound.

Effective dosages of the compounds of this invention may be easily determined by those skilled in the art following the teachings hereof and principles known to the art.

The compounds of these inventions may be administered in the form of pharmaceutical preparations including the compounds of these inventions in suitable pharmaceutical carriers to form solutions, lotions, creams, and other dosage forms known to the art. Combinations of such compounds with pharmaceutical carriers are also provided by this invention.

All publications referred to herein are hereby incorporated by reference to the extent not inconsistent herewith.

Definitions

The term "hydrocarbyl" is used herein to refer generally to organic groups comprised of carbon chains to which hydrogen and optionally other elements are attached. $CH_2$ or CH groups and C atoms of the carbon chains of the hydrocarbyl may be replaced with one or more heteroatoms (i.e., non-carbon atoms). Suitable heteroatoms include but are not limited to O, S, P and N atoms. The term hydrocarbyl includes, but is not limited to alkyl, alkenyl, alkynyl, ether, polyether, thioether, straight chain or cyclic saccharides, ascorbate, aminoalkyl, hydroxylalkyl, thioalkyl, aryl and heterocyclic aryl groups, optionally substituted tricyclic molecules, amino acid, polyalcohol, glycol, groups which have a mixture of saturated and unsaturated bonds, carbocyclic rings and combinations of such groups. The term also includes straight-chain, branched-chain and cyclic structures or combinations thereof. Hydrocarbyl groups are optionally substituted. Hydrocarbyl substitution includes substitution at one or more carbons in the group by moieties containing heteroatoms. Suitable substituents for hydrocarbyl groups include but are not limited to halogens, including chlorine, fluorine, bromine and iodine, OH, SH, $NH_2$, COH, $CO_2H$, $OR_a$, $SR_a$, $NR_aR_b$, $CONR_aR_b$, where $R_a$ and $R_b$ independently are alkyl, unsaturated alkyl or aryl groups.

The term "alkyl" takes its usual meaning in the art and is intended to include straight-chain, branched and cycloalkyl groups. The term includes, but is not limited to, methyl, ethyl, n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, and 1-methyl-1-propylbutyl. Alkyl groups are optionally substituted. Lower alkyl groups are $C_1$–$C_6$ alkyl and include among others methyl, ethyl, n-propyl, and isopropyl groups.

The term "cycloalkyl" refers to alkyl groups having a hydrocarbon ring, particularly to those having rings of 3 to 7 carbon atoms. Cycloalkyl groups include those with alkyl group substitution on the ring. Cycloalkyl groups can include straight-chain and branched-chain portions. Cycloalkyl groups include but are not limited to cyclopropyl, cyclobutyl, cyclopentyl, cyclohexyl, cycloheptyl, cyclooctyl, and cyclononyl. Cycloalkyl groups can optionally be substituted.

Aryl groups may be substituted with one, two or more simple substituents including, but not limited to, lower alkyl, e.g., methyl, ethyl, butyl; halo, e.g., chloro, bromo; nitro; sulfato; sulfonyloxy; carboxy; carbo-lower-alkoxy, e.g., carbomethoxy, carbethoxy; amino; mono- and di-lower-alkylamino, e.g., methylamino, ethylamino, dimethylamino, methylethylamino; amido; hydroxy; lower-alkoxy, e.g., methoxy, ethoxy; and lower-alkanoyloxy, e.g., acetoxy.

The term "unsaturated alkyl" group is used herein generally to include alkyl groups in which one or more carbon-carbon single bonds have been converted to carbon-carbon double or triple bonds. The term includes alkenyl and alkynyl groups in their most general sense. The term is intended to include groups having more than one double or triple bond, or combinations of double and triple bonds. Unsaturated alkyl groups include, without limitation, unsaturated straight-chain, branched or cycloalkyl groups. Unsaturated alkyl groups include without limitation: vinyl, allyl, propenyl, isopropanyl, butenyl, pentenyl, hexenyl, hexadienyl, heptenyl, cyclopropenyl, cyclobutenyl, cyclopentenyl, cyclopentadienyl, cyclohexenyl, cyclohexadienyl, 1-propenyl, 2-butenyl, 2-methyl-2-butenyl, ethynyl, propargyl, 3-methyl-1-pentynyl, and 2-heptynyl. Unsaturated alkyl groups can optionally be substituted.

Substitution of alkyl, cycloalkyl and unsaturated alkyl groups includes substitution at one or more carbons in the group by moieties containing heteroatoms. Suitable substituents for these groups include but are not limited to OH, SH, $NH_2$, COH, $CO_2H$, $OR_c$, $SR_c$, P, PO, $NR_cR_d$, $CONR_cR_d$, and halogens, particularly chlorines and bromines where $R_c$ and $R_d$, independently, are alkyl, unsaturated alkyl or aryl groups. Preferred alkyl and unsaturated alkyl groups are the lower alkyl, alkenyl or alkynyl groups having from 1 to about 3 carbon atoms.

The term "aryl" is used herein generally to refer to aromatic groups which have at least one ring having a conjugated pi electron system and includes without limitation carbocyclic aryl, aralkyl, heterocyclic aryl, biaryl groups and heterocyclic biaryl, all of which can be optionally substituted. Preferred aryl groups have one or two aromatic rings.

"Carbocyclic aryl" refers to aryl groups in which the aromatic ring atoms are all carbons and includes without limitation phenyl, biphenyl and napthalene groups.

"Aralkyl" refers to an alkyl group substituted with an aryl group. Suitable aralkyl groups include among others benzyl, phenethyl and picolyl, and may be optionally substituted. Aralkyl groups include those with heterocyclic and carbocyclic aromatic moieties.

"Heterocyclic aryl groups" refers to groups having at least one heterocyclic aromatic ring with from 1 to 3 heteroatoms in the ring, the remainder being carbon atoms. Suitable heteroatoms include without limitation oxygen, sulfur, and nitrogen. Heterocyclic aryl groups include among others furanyl, thienyl, pyridyl, pyrrolyl, N-alkyl pyrrolo, pyrimidyl, pyrazinyl, imidazolyl, benzofuranyl, quinolinyl, and indolyl, all optionally substituted.

"Heterocyclic biaryl" refers to heterocyclic aryls in which a phenyl group is substituted by a heterocyclic aryl group ortho, meta or para to the point of attachment of the phenyl ring to the decalin or cyclohexane. Heterocyclic biaryl includes among others groups which have a phenyl group substituted with a heterocyclic aromatic ring. The aromatic rings in the heterocyclic biaryl group can be optionally substituted.

"Biaryl" refers to carbocyclic aryl groups in which a phenyl group is substituted by a carbocyclic aryl group ortho, meta or para to the point of attachment of the phenyl ring to the decalin or cyclohexane. Biaryl groups include among others a first phenyl group substituted with a second phenyl ring ortho, meta or para to the point of attachment of the first phenyl ring to the decalin or cyclohexane structure. Para substitution is preferred. The aromatic rings in the biaryl group can be optionally substituted.

Aryl group substitution includes substitutions by non-aryl groups (excluding H) at one or more carbons or where possible at one or more heteroatoms in aromatic rings in the aryl group. Unsubstituted aryl, in contrast, refers to aryl groups in which the aromatic ring carbons are all substituted with H, e.g. unsubstituted phenyl (—$C_6H_5$), or naphthyl (—$C_{10}H_7$). Suitable substituents for aryl groups include among others, alkyl groups, unsaturated alkyl groups, halogens, OH, SH, $NH_2$, COH, $CO_2H$, $OR_e$, $SR_e$, $NR_eR_f$, $CONR_eR_f$, where $R_e$ and $R_f$ independently are alkyl, unsaturated alkyl or aryl groups. Preferred substituents are OH, SH, $OR_e$, and $SR_e$ where $R_e$ is a lower alkyl, i.e., an alkyl group having from 1 to about 3 carbon atoms. Other preferred substituents are halogens, more preferably chlorine or bromine, and lower alkyl and unsaturated lower alkyl groups having from 1 to about 3 carbon atoms. Substituents include bridging groups between aromatic rings in the aryl group, such as —$CO_2$—, —CO—, —O—, —S—, —P—, —NH—, —CH=CH— and —$(CH_2)R$— where R is an integer from 1 to about 5, and particularly —$CH_2$—.

Examples of aryl groups having bridging substituents include phenylbenzoate. Substituents also include moieties, such as —(CH$_2$)$_R$—, —O—(CH$_2$)$_R$— or —OCO—(CH$_2$)$_R$—, where R is an integer from about 2 to 7, as appropriate for the moiety, which bridge two ring atoms in a single aromatic ring as, for example, in a 1, 2, 3, 4-tetrahydronaphthalene group. Alkyl and unsaturated alkyl substituents of aryl groups can in turn optionally be substituted as described supra for substituted alkyl and unsaturated alkyl groups.

The terms "alkoxy group" and "thioalkoxy group" (also known as mercaptide groups, the sulfur analog of alkoxy groups) take their generally accepted meaning. Alkoxy groups include but are not limited to methoxy, ethoxy, n-propoxy, isopropoxy, n-butoxy, sec-butoxy, isobutoxy, tert-butoxy, n-pentyloxy, neopentyloxy, 2-methylbutoxy, 1-methylbutoxy, 1-ethyl propoxy, 1,1-dimethylpropoxy, n-hexyloxy, 1-methylpentyloxy, 2-methylpentyloxy, 3-methylpentyloxy, 4-methylpentyloxy, 3,3-dimethylbutoxy, 2,2-dimethoxybutoxy, 1,1-dimethylbutoxy, 2-ethylbutoxy, 1-ethylbutoxy, 1,3-dimethylbutoxy, n-pentyloxy, 5-methylhexyloxy, 4-methylhexyloxy, 3-methylhexyloxy, 2-methylhexyloxy, 1-methylhexyloxy, 3-ethylpentyloxy, 2-ethylpentyloxy, 1-ethylpentyloxy, 4,4-dimethylpentyloxy, 3,3-dimethylpentyloxy, 2,2-dimethylpentyloxy, 1,1-dimethylpentyloxy, n-octyloxy, 6-methylheptyloxy, 5-methylheptyloxy, 4-methylheptyloxy, 3-methylheptyloxy, 2-methylheptyloxy, 1-methylheptyloxy, 1-ethylhexyloxy, 1-propylpentyloxy, 3-ethylhexyloxy, 5,5-dimethylhexyloxy, 4,4-dimethylhexyloxy, 2,2-diethylbutoxy, 3,3-diethylbutoxy, 1-methyl-1-propylbutoxy, ethoxymethyl, n-propoxymethyl, isopropoxymethyl, sec-butoxymethyl, isobutoxymethyl, (1-ethylpropoxy)methyl, (2-ethylbutoxy)methyl, (1-ethylbutoxy)methyl, (2-ethylpentyloxy)methyl, (3-ethylpentyloxy)methyl, 2-methoxyethyl, 1-methoxyethyl, 2-ethoxyethyl, 3-methoxypropyl, 2-methoxypropyl, 1-methoxypropyl, 2-ethoxypropyl, 3-(n-propoxy)propyl, 4-methoxybutyl, 2-methoxybutyl, 4-ethoxybutyl, 2-ethoxybutyl, 5-ethoxypentyl, and 6-ethoxyhexyl. Thioalkoxy groups include but are not limited to the sulfur analogs of the alkoxy groups specifically listed supra.

"Optional" or "optionally" means that the subsequently described event or circumstance may or may not occur, and that the description includes instances where said event or circumstance occurs and instances in which it does not. For example, "optionally substituted phenyl" means that the phenyl radical may or may not be substituted and that the description includes both unsubstituted phenyl radicals and phenyl radicals wherein there is substitution.

"Amino acids" as used herein include naturally occurring and commercially available amino acids and optical isomers thereof. Typical natural and commercially available amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, o-, m-, and p-tyrosine, tryptophan, glutamine, asparagine, proline and hydroxyproline. "Amino acid" as used herein includes amino acid residues and amino acid side chains. An "amino acid residue" is an amino acid radical —NHCH(R)C(O)—, wherein R is an amino acid side chain, except for the amino acid residues of proline and hydroxyproline which are —N(CH$_2$—CH$_2$—CH$_2$)CHC(O)— and —N(CH—CHOHCH$_2$)CHC(O)—, respectively. An amino acid side chain is a radical found on the α-carbon of an α-amino acid as defined herein, where the radical is either hydrogen (side chain of glycine), methyl (side chain of alanine), or is a radical bonded to the α-carbon by a methylene (—CH$_2$—), or phenyl group.

"Contacting" reaction components with each other refers to providing a medium and/or reaction chamber in which the reaction components are placed together so that they can react with each other. Preferably, the reaction components are suspended or dissolved in a carrier fluid which is a liquid medium. "Maintaining reaction components in contact" means keeping the components together in such a way that they can react with each other.

"Straight chain or cyclic saccharides" include mono-, di- and poly-, straight chain and cyclic saccharides that are optionally substituted with an amino group which is optionally acetylated. Straight chain saccharides that are useful in this invention include but are not limited to those molecules with a chain of 5 or 6 carbon atoms with one or more —OH groups attached, and either an aldehyde or ketone group. Cyclic saccharides are saccharides that are in a ring form. Disaccharides are compounds wherein two monosaccharide groups are linked. Polysaccharides are compounds wherein more than two monosaccharide groups are linked. Specific examples of saccharides useful in this invention include glucose, ribose and glucosamine, among others.

Substituents which impart water solubility include but are not limited to alcohols; polyalcohols; straight chain or cyclic saccharides; amines and polyamines; sulfate groups; phosphate groups; ascorbate groups; alkyl chains optionally substituted with —OH at any position; glycols, including polyethylene glycols, and polyethers.

Tricyclic compounds include all compounds having three saturated, unsaturated or partially saturated six-membered rings, preferably as depicted herein, with substituents as defined herein.

This invention is also directed to pharmaceutically acceptable esters and salts of the tricyclic compounds of the various formulas and structures disclosed herein. Acid addition salts are prepared by contacting compounds having appropriate basic groups therein with an acid whose anion is generally considered suitable for human or animal consumption. Pharmacologically acceptable acid addition salts include but are not limited to the hydrochloride, hydrobromide, hydroiodide, sulfate, phosphate, acetate, propionate, lactate, maleate, malate, succinate, and tartrate salts. All of these salts can be prepared by conventional means by reacting, for example, the selected acid with the selected basic compound. Base addition salts are analogously prepared by contacting compounds having appropriate acidic groups therein with a base whose cation is generally considered to be suitable for human or animal consumption. Pharmacologically acceptable base addition salts, include but are not limited to ammonium, amine and amide salts.

Pharmaceutically acceptable esters of compounds of this invention are prepared by conventional methods, for example by reaction with selected acids. Pharmaceutically acceptable esters include but are not limited to carboxylic acid esters RCOO-D (where D is a cationic form of a compound of this invention and where R is H, alkyl or aryl groups).

This invention is also directed to prodrugs and derivatives which on being metabolized will result in any of the effective tricyclic aldose reductase inhibitors of this invention. For example, alkoxy or acetate groups can be metabolized to hydrogens. Labile substituents may be protected employing conventional and pharmaceutically acceptable protecting groups removable on metabolism. Pharmaceutically active compounds may be derivatized by conventional methods to provide for extended metabolic half-life, to enhance solubility in a given carrier, to provide for or facilitate slow-release or timed-release or enhance or affect other drug delivery properties.

Pharmaceutical compositions according to the present invention comprise one or more tricyclic compounds, salts or esters of this invention in association with a pharmaceutically acceptable carrier or excipient adapted for use in human or veterinary medicine. Such compositions may be prepared for use in conventional manner in admixture with one or more physiologically acceptable carriers or excipients. The compositions may optionally further contain one or more other therapeutic agents. The compounds, salts or esters of this invention are present in these pharmaceutical compositions in an amount or in a combined amount sufficient to elicit a measurable positive effect on a symptom or condition associated with aldose reductase or a measurable physiological effect.

The tricyclic compounds, salts and esters of this invention may be formulated for oral, buccal, parenteral, topical or rectal administration. In particular, they may be presented in unit dose form. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g. sterile, pyrogen-free water, before use.

The pharmaceutical compositions according to the invention may also contain other active ingredients, such as antimicrobial agents, or preservatives.

The invention further provides a process for preparing a pharmaceutical composition which comprises bringing a tricyclic aldose reductase inhibitor of the invention into association with a pharmaceutically acceptable excipient or carrier. The carrier or excipient being selected as is known in the art for compatibility with the desired means of administration, for compatibility with the selected compounds and to minimize detrimental effects to the patient.

The magnitude of a prophylactic or therapeutic dose of a particular compound will, of course, vary with the nature of the severity of the condition to be treated, the particular tricyclic aldose reductase inhibitor and its route of administration. It will also vary according to the age, weight and response of the individual patient, all as will be readily ascertainable to those skilled in the art.

The compounds of the present invention are preferably formulated prior to administration. The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. The compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The term "unit dosage form" refers to physically discrete units suitable as unitary dosages for patients, including human subjects and other mammals, each unit containing a predetermined quantity of active material calculated to produce the desired therapeutic effect, in association with a suitable pharmaceutical carrier.

This invention is further directed to therapeutic methods employing the tricyclic aldose reductase inhibitors of this invention and pharmaceutical compositions containing them in the treatment of disorders or physiological conditions involving disorders due to the activity and presence of aldose reductase. These methods comprise a step of administering to a patient having the disorder or symptoms thereof a pharmaceutical composition comprising one or a mixture of the compounds, salts or esters of this invention where the compounds, or mixtures of compounds of this invention are present in the composition at a level or a combined level sufficient to effect a positive biological response (an "effective amount"). The present invention provides aldose reductase inhibitors that can be used in place of or in combination with currently known pharmaceuticals active against disorders such as cataract and diabetic retinopathy. Certain compounds of this invention can exhibit improved properties (enhanced activity and/or decreased undesired side-effects) for treatment of such disorders as compared to previously known compounds useful for such treatments.

DETAILED DESCRIPTION OF THE INVENTION

Bioactivity Assays

Figure 1A:
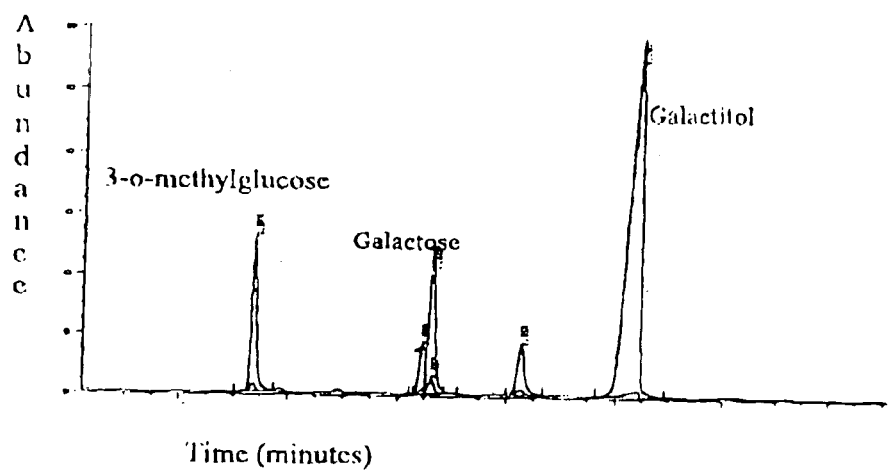
FIG. 1A shows the GC plot of polyol fraction from lens epithelial cells grown for 48 hours in 40 mM galactose [Peak 1 at 6.6 minute is 3-O-methylglucose (a standard was added for quantification of the other peaks); Peak 2 at 7.25 minute is galactose; Peak 3 at 8 minute is galactitol (the polyol)].

The activity of the drugs is tested in various ways, including tissue culture assays and assays testing aldose reductase inhibition. For the tissue culture assay, a lens epithelial cell line is grown in galactose with or without the drug. Cells are tested for polyol accumulation by GC/mass spectrometry. Levels of PKC are tested in homogenized cell pellets or in samples of lens, retina or sciatic nerves from treated patients. Tissue is homogenized and tested for PKCγ levels using Western blots. These procedures are described in more detail below.

Human aldose reductase (AR) was obtained from over-expression of the human AR gene in an *E coli* system and was purified by column chromatography using a talon metal affinity column and eluted with a gradient mixture of Tris, NaCl buffer and imidazole solution. The human AR inhibition assay was conducted as follows. In a sample cuvette, 25 mM of D-xylose (75 mg/mL) and 0.15 mM of reduced nicotinamide adenine dinucleotide phosphate (NADPH) (4 mg/mL), and various amount of the inhibitor [in PBS (phosphate buffer saline) solution; the concentration of the inhibitor was determined using UV spectroscopy based on $\epsilon_{max}$ at $\lambda_{max}$ of the drug] in 700 uL of PBS (a solution made of 1.44 g of $Na_2HPO_4$, 0.24 g $KH_2PO_4$, 0.2 g KCl, and 8 g NaCl in 1 L of distilled water) buffer (pH=6.1) solution and 200 uL of the AR enzyme (a final volume of 1 mL was obtained). The intensity of absorption of NADPH ($\lambda_{max}$=340 nm) was measured. When xylose is reduced to xylitol, NADPH is converted into NADP and the absorption at 340 nm decreases. When AR is inhibited by the drug, the absorption at 340 nm of NADPH remains unchanged. Each assay was repeated three times and an average $IC_{50}$ value was obtained. Several tricyclic pyrones were tested for the inhibition of AR along with Toirestat (obtained from Ayerst Laboratories Research, Inc., Princeton, N.J.) and Sorbinil (obtained from the procedure given in *Structure* 1997, 5, 601–612) and the data are summarized in Table 3. Contrary to Toirestat, compounds 1 and 2 are water soluble materials. As shown, compound 1 has greater inhibitory activity than Tolrestat and Sorbinil.

TABLE 3

Inhibition of Human Retina Aldose Reductase.

| Inhibitor | Compound 1 | Compound 2 | Tolrestat | Sorbinil |
| --- | --- | --- | --- | --- |
| $IC_{50}$ | 2 nM | 20 nM | 5 nM | 2 µM |

Compounds 1 and 2 (up to 100 uM) have been added to bovine lens epithelial cells and no toxicity was found.

The enzyme assay was also performed for other compounds, as shown in Table 4.

TABLE 4

$IC_{50}$ values obtained from the enzyme assay (aldose reductase)

| Compound | $IC_{50}$ |
| --- | --- |
| 1 | 0.002 µM |
| 3 | >500 µM |
| 2 | 0.020 µM |
| 5c | 200 µM |
| 6 | No significant inhibition detected |
| 7 | No significant inhibition detected |

The ability of the drugs to inhibit galactitol formation from galactose was also studied in N/N 1003 lens epithelial cells. Two sets of lens cells were grown in media with (control) or without 40 mM galactose. Various concentration of inhibitors were added initially and the cells were grown for 48 hours. The cells were lysed and galactose and galactitol were extracted out and the concentrations were determined using gas chromatography and mass spectrometry by silylating the crude extract with excess of trimethylsilyl chloride, trimethylsilyl imidazole and pyridine at 70° C. for 1 h. The results are summarized in Tables 5 and 6.

TABLE 5

% galactitol for varying concentrations of compound 1

| Concentration of 1 (uM) | % galactitol |
| --- | --- |
| 1 | 80 |
| 10 | 30 |

TABLE 6

% galactitol for varying concentrations of Tolrestat

| Concentration of Tolrestat (uM) | % galactitol |
| --- | --- |
| 0.5 | 100 |
| 1 | 90 |
| 7 | 53 |

Figure 1B:
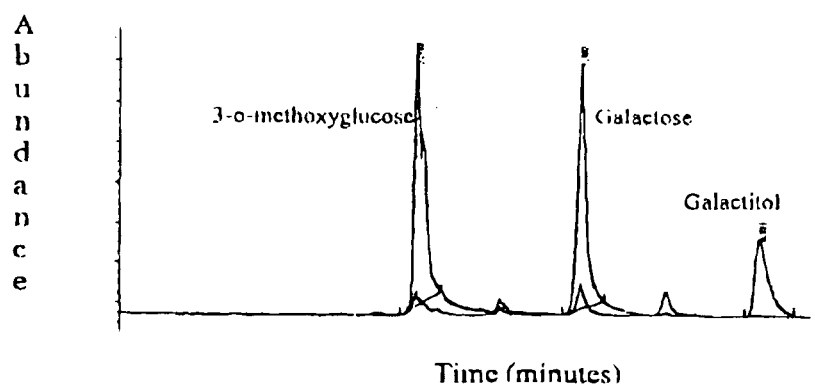
FIG. 1B shows the GC plot of polyol fraction from lens epithelial cells grown for 48 hours in 40 mM galactose and 10 uM compound 1 [Peak 1 at 6.6 minute is 3-O-methylglucose (a standard was added for quantification of the other peaks); Peak 2 at 7.25 minute is galactose; Peak 3 at 8 minute is galactitol (the polyol)]

FIG. 1A is the GC/MS data showing the relative galactose and galactitol contents for lens epithelial cells grown for 48 hours in 40 mM galactose. Peak 1 at 6.6 minute is 3-O-methyglucose (a standard was added for quantification of the other peaks); Peak 2 at 7.25 minute is galactose; Peak 3 at 8 minute is galactitol (the polyol). FIG. 1B is the GC/MS data showing the relative galactose and galactitol contents for lens epithelial cells grown for 48 hours in 40 mM galactose and 10 uM compound 1. As shown is the figure, addition of compound 1 decreases the concentration of galactitol relative to galactose.

TABLE 7

Results of tissue culture assay of inhibitors 1, 2, 3, and 5c (the number of trials is in parenthesis)

| Inhibitor (10 uM) | % inhibition |
| --- | --- |
| 1 | 80 ± 10 (3) |
| 3 | <10 (2) |
| 2 | <10 (2) |
| 5c | 43 ± (2) |
| Tolrestat | 95 ± 4 (3) |

Table 7 shows results of tissue culture assay of inhibitors 1, 2, 3, and 5c. 40 mM galactose media was supplemented with 10 uM inhibitor and fed to lens epithelial cells for 48 hours.

The $IC_{50}$ values for compound 1 is 6 uM (in lens cells) and for Tolrestat is 8 uM. These data shows that compound 1 is a slightly better AR inhibitor than Tolrestat. Since Tolrestat is insoluble in water, in the lens cells study, the sodium salt of Tolrestat was made by treating with NaOH and used. On the other hand, compound 1 is water soluble and was used as it is.

Computational Docking Experiments

Computational docking experiments of various synthesized materials (such as 1 and 2) and other structures with aldose reductase (the X-ray structure is known: see Urzhumtsev, A. et al. A 'specificity' pocket inferred from the crystal structures of the complexes of aldose reductase with the pharmaceutically important inhibitors tolrestat and sorbinil. *Structure* 1997, 5, 601–612) were performed. A tight binding between the inhibitor and AR (binding energy, $K_r=-77$ Kcal/mol), and hydrogen bonding between the carboxylic acid group of 1 with residues His110 (2.81 Å) and Trp111 (2.76 Å) of AR were found (data not shown). Computer docking experiments show that other derivatives such as compounds 5–14 have similar or better binding energies than 1. Therefore, they would be expected to inhibit aldose reductase activity to a similar or greater extent as 1.

Diabetic Rat Model

An 8 week study to determine the effects of streptozotocin diabetes on vascular leakage as measured by fluorophotometry, retinal ultrastructure as measured by electron miscoscopy, and on PKC levels as measured by Western blot has been completed. Diabetes was monitored by blood glucose levels. The fluorophotometry was measured using an instrument which is available in the Veterinary School Ophthalmology Department which has been adapted for rats. Vascular leakage was measured during the 8 week period to determine the effects of AR inhibitors. Eyes from the diabetic and normal animals were fixed and processed at the Pathology Facility and retinal ultrastructure was determined. The photoreceptors of diabetic animals are swollen, disorganized and reduced in length. The outer-nuclear layer was about one-half the distance from the RPE in the diabetic rats compared to the distance in the healthy rats. The diabetic rat photoreceptor depth was reduced by 55–60% compared to healthy photoreceptors. The RPE was also altered in structure but no change in phagosome number was noted. PKC levels were increased as shown by both enzyme assays and by Western blots.

In order to test for in vivo effects of ARI's, rats were fed a 40% galactose diet for 9 days and the accumulation of galactitol was measured in lens tissue. This tissue has high aldose reductase activity and the eye has a separate vasculature. Thus, if the ARI works in the lens this is a good indication that the drug works and can penetrate to most tissues.

The specific experimental details follow. Six-week-old Spraque Dawley Rats (250–300 g) were fed normal chow (Bioserve rodent grain base diet 50% fiber F3975), high galactose chow (Bioserve Rodent grain base diet 50% galactose F1624), normal chow with inhibitor, or high galactose chow with either the inhibitor (100 mg/Kg body weight per day) or Tolrestat (100 mg/Kg body weight per day). The rats were given food supplemented with inhibitor in the morning and then given food and water ad libitum the rest of the day. They were kept on a 12-hour on and 12-hour off light cycle. After 9 days, the rats were sacrificed with an overdose of $CO_2$ and then eyes were taken and immediately frozen on dry ice for later polyol and PKC analyses. Experiments on all rats conformed to the ARVO resolution on the Use of Animals in Research.

Polyol Content:

The lenses were removed and weighed. They were placed in 500 µL of PBS supplemented with 15 µL of 3-O-methoxyglucocse as internal standard. The lenses were then boiled for 20 minutes and 100 µL of 0.3 M zinc sulfate and 100 µL of barium sulfate were added. The mixture was centrifuged for 15 minutes at 10,000 g. The supernatant was removed and lyophilized for GC/MS analysis.

PKC Analysis of Diabetic and Galactosemic Rat Lens:

The lenses were removed from the enucleated eyes and weighed. They were put in 200 µL lysis buffer (50 mM Tris, 100 mM NaCl, M-Per Pierre Zwitterionic detergent, 5 mM NaF, 1 mM $Na_3VO_4$, 40 mM β-glycerophosphate, 6 µg/mL chymotrypsin, 10 µM 3,4-dichlorocoumarin, 10 µM E-64, 1 µg/mL leupeptin, 1 µg/mL pepstatin A, 1 µg/mL aprotinin, 1 mM PMSF, and 5 mM EDTA (Sigma). The lenses were then ground using a tissue grinder until they were a uniformly white solution. They were then sonicated to make certain all the cells were disrupted. The mixture was then centrifuged for 20 minutes at 0° C. at 3 g. The supernatant was then analyzed for protein content using BSA assay (Pierce). Equal amounts of protein were loaded and separated on a 10% SDS polyacrylamide gel. The proteins were transferred to nitrocellulose (Midwest Scientific; pore size 0.45 µm). The western was blocked with a 3% milk solution, and then mouse anti-PKC γ (1:5000) or PKC α (1:1000) antisera (Transgenic Laboratories) were applied in a 3% milk solution overnight. The membrane was then washed 3 times in TDN (0.05 M NaCl, 2 mM EDTA, 0.01 M Tris) and goat anti-mouse antisera IgG (1:5000 Promega) was applied. The autoradiogram was developed using supersignal chemiluminescent substrate from Pierce.

Figure 2:
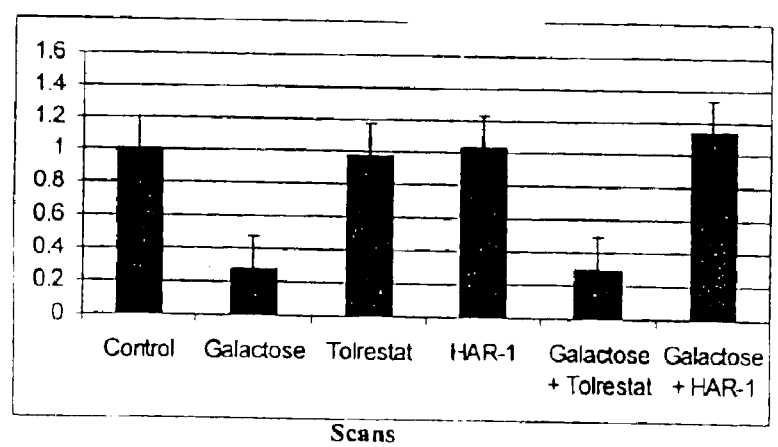
FIG. 2 shows PKC-γ content in lens epithelial cells of control, Galactose, tolrestat, compound 1 (HAR1), tolresiat/Galactose, and compound 1/galactose rats.

Lens epithelial cells exposed to 40 mM galactose exhibit a 50% decrease in PKC-γ. The effects of streptozotocin induced diabetes on PKC-γ levels in rat lens have been measured. The rat lens of diabetic animals show a 50–70% decrease in PKC-γ levels (data not shown). Rats exposed to 40% galactose for 9 days also had reduced PKC-γ levels as demonstrated by Western blots and when compared to rats fed a control diet. The galactose-fed animals were also fed with 100 mg/Kg body weight per day of compound 1 or Tolrestat. FIG. 2 shows the PKC-γ content in lens epithelial cells of control, Galactose, tolrestat, compound 1 (HAR1), tolrestat/Galactose, and compound 1/galactose rats. It is seen that the PKC-γ levels remain high when compound 1 is used.

Figure 3A:
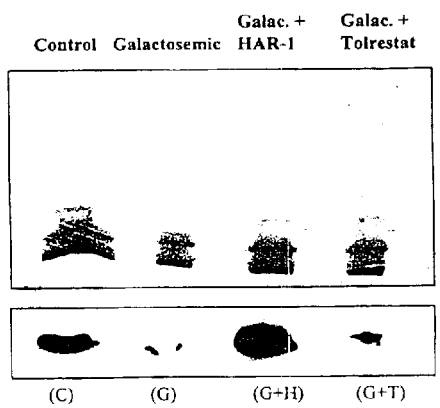
FIG. 3 shows data for lens cells (3A) and sciatic nerve cells (3B) of diabetic rats under various conditions.
Figure 3B:
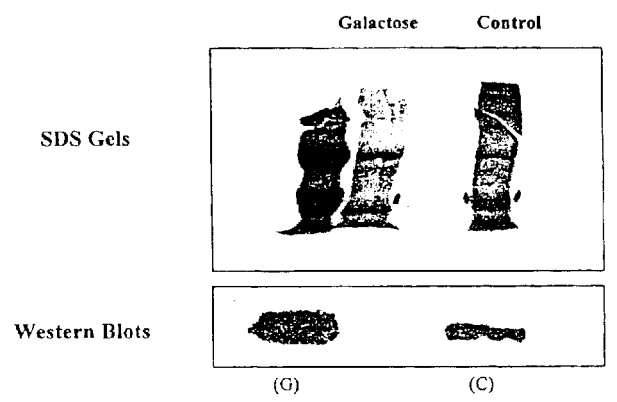
Figure 3B:
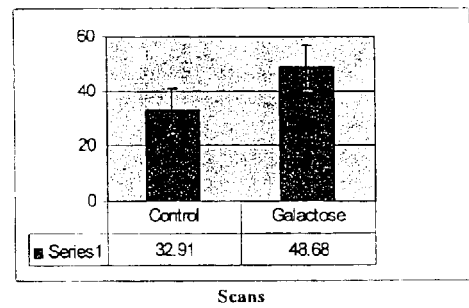

The results are shown in FIG. 3A for the lens cells which shows that when the animals were fed 40% galactose feed, the lens epithelial cell PKC-γ decreased, and when the animals were given compound 1 or Tolrestat with the high galactose feed, the PKC-γ levels remained near normal (control levels). Moreover, pathology studies indicate that the drug is not toxic to the rats. FIG. 3B shows Western blots for sciatic nerve cells which indicate that the PKC-γ levels were decreased in these animals and that this was normalized when fed with compound 1 or Tolrestat and compound 1 provided a greater level of normalization than Tolrestat. The lower graph in FIG. 3B shows the readout intensities from the upper graph.

Canine Study

Figure 4:
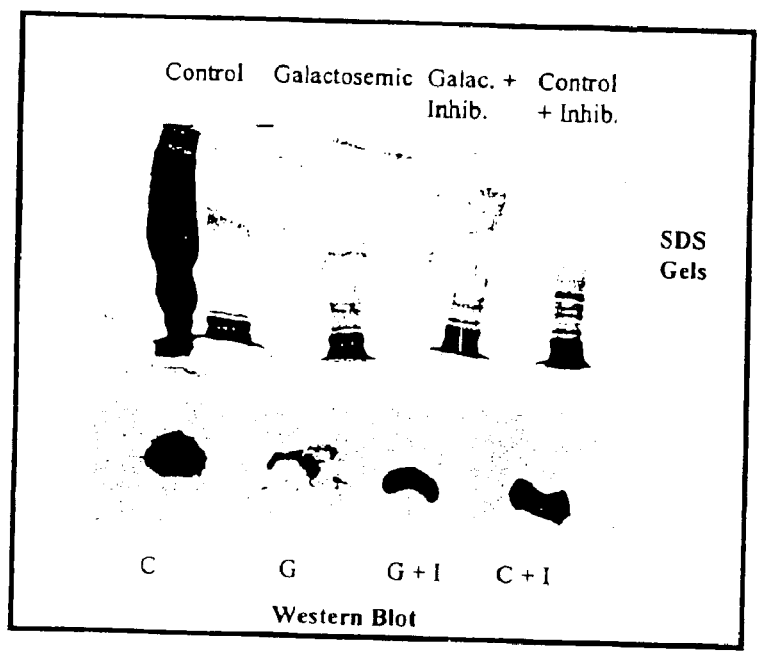
FIG. 4 shows SDS gels and Western blots illustrating the effects of compound 1 in lens cells of diabetic dogs.
Figure 5:
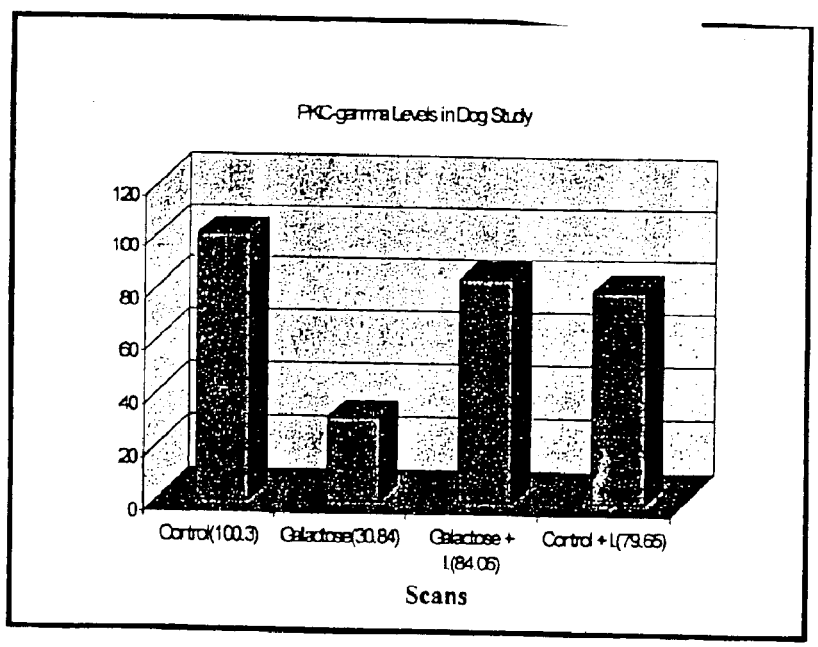
FIG. 5 shows PKC-gamma levels in the lenses of control dogs, dogs fed a galactose-rich diet, dogs fed a galactose-rich diet and treated with compound 1, and control dogs treated with compound 1.

A pilot study was conducted to determine initial toxicity and efficacy in a Beagle model. The study was conducted at the fully accredited facility at the Kansas State University Veterinary Clinic. The dogs were fed a 40% galactose diet for 6 weeks. These dogs developed cataracts. Compound 1 was administered orally at 100 mg/kg body weight/day for 6 weeks. At this dose, the polyol levels were 50% normalized (FIG. 4) and PKCγ levels were 80% normalized (FIG. 5). FIG. 4 shows the results of the Western Blot of the PKC-γ level of dog lens from control (C; normal dogs), treated with galactose (G), galactose and inhibitor 1 (G+I) and control with inhibitor 1 (C+I). As shown, the PKC-γ levels of the control, G+I and C+I are similar but levels of G are significantly decreased. FIG. 5 shows the read-out of intensities of PKC-γ levels from FIG. 4. The PKC-γ levels of dogs treated with galactose is 30.8%, G+I is 84.1% and C+I is 79.7%. The GC/MS data of the level of polyol in dog lens is shown in Table 8. Additional testing at higher doses is planned to determine optimal dose for efficacy with no or low toxicity. These experiments are well within the skill and experience of one of ordinary skill in the art and can be performed without undue experimentation.

TABLE 8

| Galactosemic | Galactose | Galactitol (polyol) |
|---|---|---|
| With inhibitor | 72.7% | 27.3% |
| Without inhibitor | 43.3% | 56.7% |

Synthesis

A class of new compounds; namely, 1H,7H-5a,6,8,9-tetrahydro-1-oxopyrano[4,3-b][1]benzopyranes, has been synthesized from a one-pot condensation of 6-substituted 4-hydroxy-2-pyrones and cyclic α-enals in high yields. The chemistry has been reported in several publications (see Hua, D. H., et al. A One-Pot Condensation of Enals and Pyrones. Synthesis of Novel 1H,7H-5a,6,8,9-Tetrahydro-1-oxopyrano[4,3-b][1]benzopyrans. *J. Org. Chem.* 1997, 62, 6888–6896; Hua, D. H. et al (5aS,7S)-7-Isopropenyl-3-methyl-1H,7H-5a,6,8,9-tetrahydro-1-oxopyrano[4,3-b][1] benzopyran. *Aca Cryst.* 1997, C53, 1995–1997) For example, treatment of pyrone 20 (commercially available) with 1 equiv of cyclohexenecarboxaldehyde (21) and 0.5 equiv of L-proline in ethyl acetate at 70° C. for 12 h afforded a 76% yield of tricyclic pyrone 23 (Scheme 1). Significantly, when (S)-(−)-perillaldehyde (22; commercially available) was used, a single enantiomer, 24 (78% yield), was isolated. These compounds were identified by spectroscopic data and single-crystal X-ray crystallography (see Hua, D. H.; Chen, Y.; Robinson, P. D.; Meyers, C. Y. (5aS,7S)-7-Isopropenyl-3-methyl-1H,7H-5a,6,8,9-tetrahydro-1-oxopyrano[4,3-b][1] benzopyran. *Acta Cryst.* 1997, C53, 1995–1997). Compound 24 and all compounds that contain C-7 substituents are optically pure. It should be noted that the enantiomer of 22 had been prepared by us from the oxidation of (R)-(+)-perillyl alcohol (commercially available) with Dess-Martin periodinane (85% yield) (Dess, D. B.; Martin, J. C. Readily accessible 12-I-5 oxidant for the conversion of primary and secondary alcohols to aldehydes and ketones. *J. Org. Chem.*, 48, 4155–4156, 1983).

Hence, the enantiomer of 22 can be synthesized from the condensation reaction using (R)-(+)-perillaldehyde. The carboxylic acid group was readily introduced by treating pyrone 23 and 24 separately with lithium diisopropylarnide (LDA) in THF followed by $CO_2$ gas and then HCl (Scheme 2). Compounds 1 (94% yield) and 6 (90% yield), respectivelly, were obtained.

Scheme 1

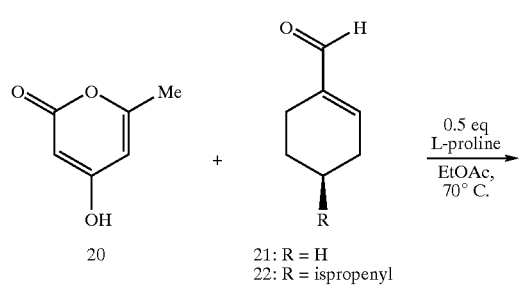

20
21: R = H
22: R = ispropenyl

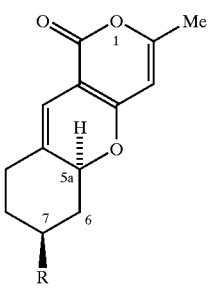

23: R = H (76% yield)
24: R = ispropenyl (78% yield)

Scheme 2

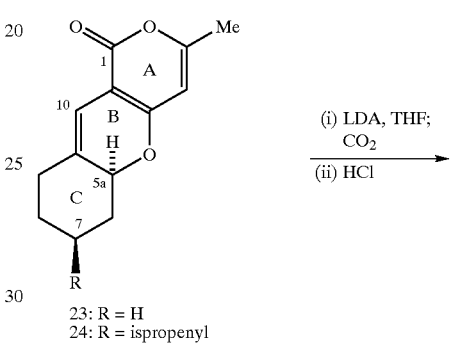

23: R = H
24: R = ispropenyl (i) LDA, THF; $CO_2$
(ii) HCl

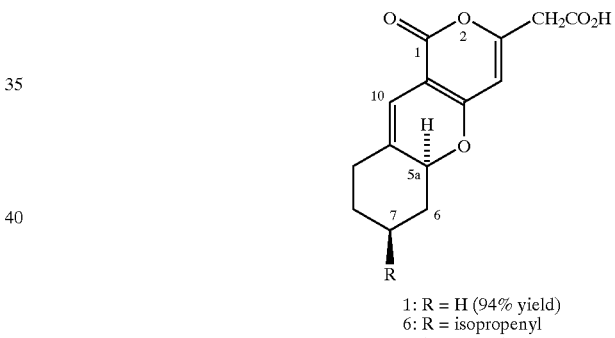

1: R = H (94% yield)
6: R = isopropenyl (90% yield)

Large quantity (~2 grams) of compound 1 have been prepared for animal studies.

Compound 3 was produced from 23 by the sequence: (i) treatment with LDA followed by n-butyl glyoxylate (87% yield); and (ii) basic hydrolysis of the ester function of intermediate 25 with 1% NaOH followed by acidification with HCl (91% yield) (Scheme 3). Carboxylic acid 2 was produced by the hydroboration of the C-10 double bond of 25 with borane THF followed by 30% $H_2O_2$ and 0.1% NaOH and then basic hydrolysis with NaOH.

Scheme 3

23 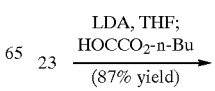

LDA, THF;
HOCCO$_2$-n-Bu
(87% yield)

23

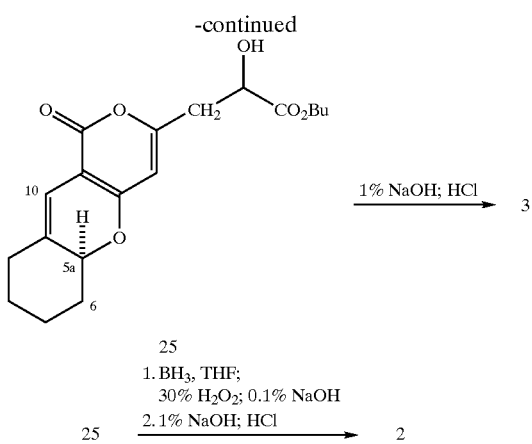

25

1. BH₃, THF;
   30% H₂O₂; 0.1% NaOH
2. 1% NaOH; HCl

→ 2

To alter the length of the tether carboxylic acid group attached at C-3 of the tricyclic pyrone, we also synthesized carboxylic acid 4 by a sequence: (i) deprotonation of pyrone 23 with LDA in THF followed by MoO₅.HMPA.pyridine (Vedejs, E.; Engler, D. A.; Telshow, J. E. *J. Org. Chem.* 1978, 43, 188); (ii) oxidation of the resulting alcohol 26 with Dess-Martin periodinane in methylene chloride; and (iii) oxidation of the resulting aldehyde 27 with silver oxide in acetonitrile (Scheme 4).

Scheme 4

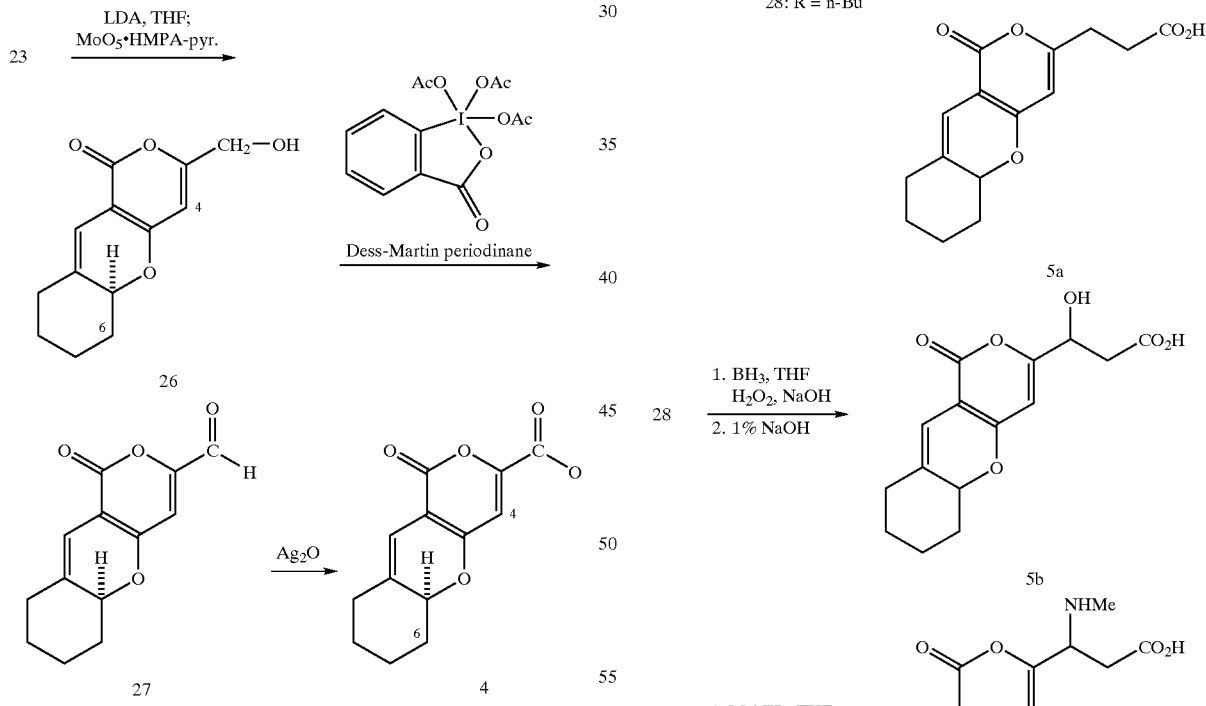

Compounds 5a, 5b, and the derivative of 5c were synthesized from alcohol 25 as outlined in Scheme 5. Hence, mesylation of alcohol 25 with methanesulfonyl chloride and triethylamine in methylene chloride followed by elimination with 1,8-diazabicyclo[5.4.0]undec-7-ene (DBU) in toluene gave a 69% yield of ene ester 28. Selective reduction of the side chain alkene of 28 with diimide followed by basic hydrolysis of the butyl ester function afforded carboxylic acid 5a. The side chain alkene of 28 was also selectively reacted with borane in THF followed by 30% hydrogen peroxide and 0.1% NaOH and the basic hydrolysis to give β-hydroxy carboxylic acid 5b. Michael-type addition of ene ester 28 with methylamine in THF at 0° C. followed by basic hydrolysis generated amino acid 29. Compounds 5a, 5b, and 29 are all water soluble materials.

Scheme 5

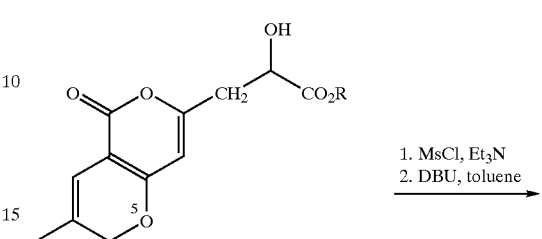

25: R = n-Bu (87% yield)

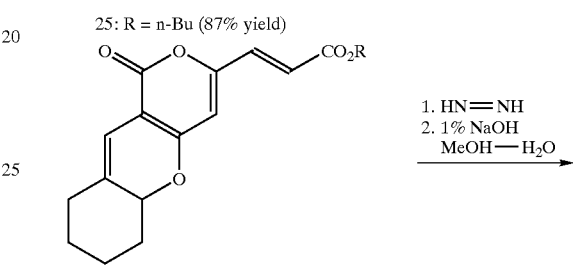

28: R = n-Bu

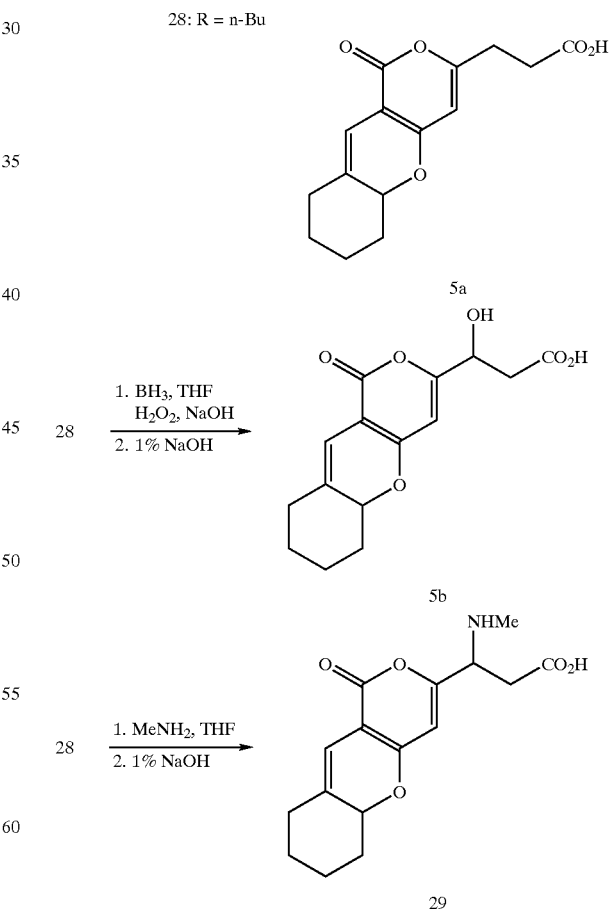

Carboxylic acid 7 was synthesized from tricyclic pyrone 24 (Scheme 6). Hence, formylation of 24 with LDA in THF at −78° C. followed by benzyl chloroformate gave an 83% yield of ester 30. Selective hydroboration of the C-11 double bond of 30 with 1 equiv of borane in THF at 0° C. followed by oxidation with 30% hydrogen peroxide and 0.1% NaOH afforded a 69% yield of alcohol 31. Basic hydrolysis of ester 31 with 1% NaOH in MeOH and water provided acid 7 (89% yield).

chloride to produce aldehyde 33 and was then oxidized further with silver oxide to give carboxylic acid 9 (Scheme 7).

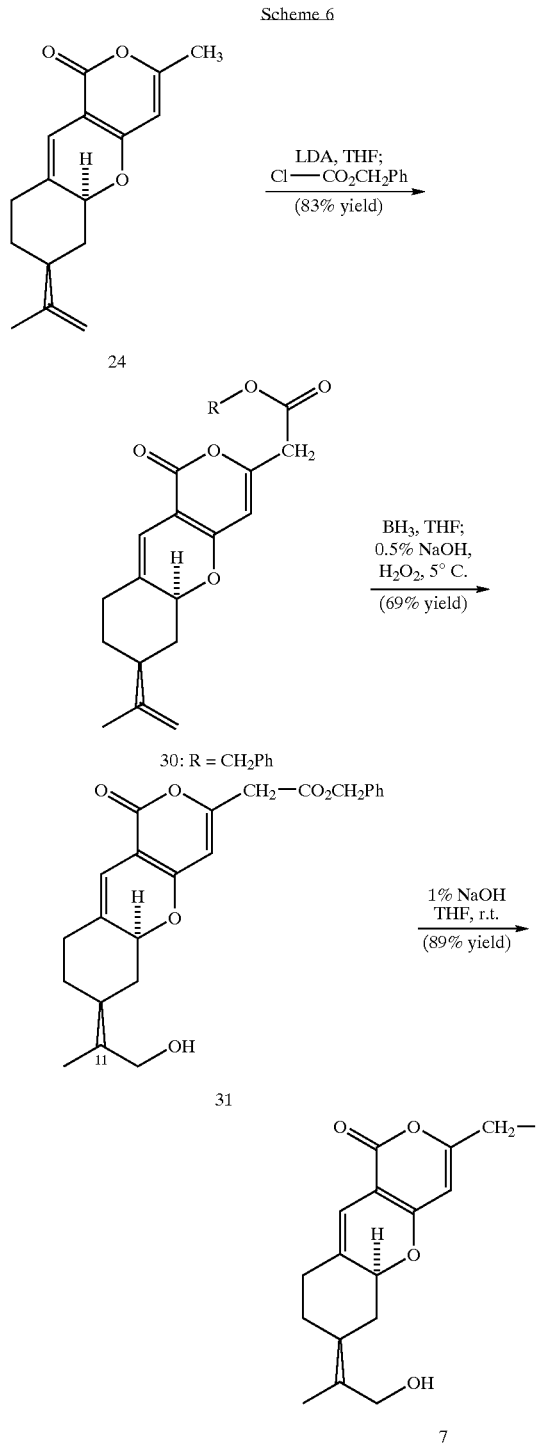

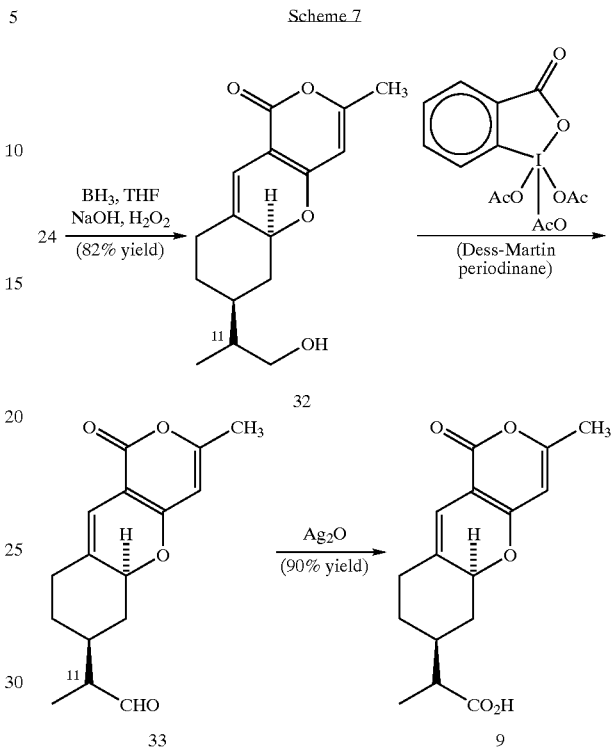

4-Hydroxy-6-methyl-2-pyridinone (34) has been synthesized from the cyclization of ethyl 5-amino-3-oxo-4-hexenoate (35) (Scheme 8). This pyridinone will be used to synthesize analogs 11~14. Amine 35 was prepared from the addition reaction of the dianion of ethyl acetoacetate with acetonitrile.

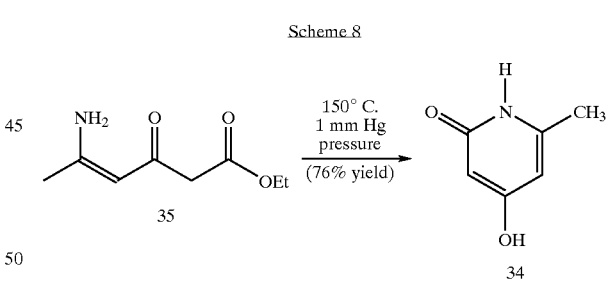

Carboxylic acid 9 has been synthesized by the selective hydroboration of tricyclic pyrone 24 with 1 equiv of borane in THF followed by 0.1% NaOH and 30% $H_2O_2$ (82% yield) to give alcohol 32. This alcohol was subjected to oxidation with the Dess-Martin periodinane reagent in methylene Other nitrogen analogs of tricyclic pyrone 23 such as 34 and 35 were also prepared. These pyrones can be converted into the corresponding C-3 acetic acids by a similar method as that for the formation of compound 1. Hence, condensation of 4-amino-6-methylpyrone (39) (Cervera, M.; Moreno-Manas, M.; Pleixats, R. *Tetrahedron* 1990, 46, 7885–7892) with aldehyde 21 and (S)-10-camphorsulfonic acid in toluene at 85° C. gave tricyclic pyrone 34 and pyranoisoquinoline 35 (Scheme 9). Amino pyrone 39 was prepared by following the reported procedure in Cervera, M.; Moreno-Manas, M.; Pleixats, R. *Tetrahedron* 1990, 46, 7885–7892.

Similarly, analogs that modified the C-7 side chain such as compounds 41~43 were also made (Scheme 10). Mesylation of alcohol 32 with methanesulfonyl chloride and triethylamine in methylene chloride gave a 78% yield of mesylate 40. Displacement of 40 with sodium salt of adenine or 3-deazaadenine or potassium phthalimide gave good yields of adenine analog 41, 3-deazaadenine analog 42, and phthalimide analog 43, respectively.

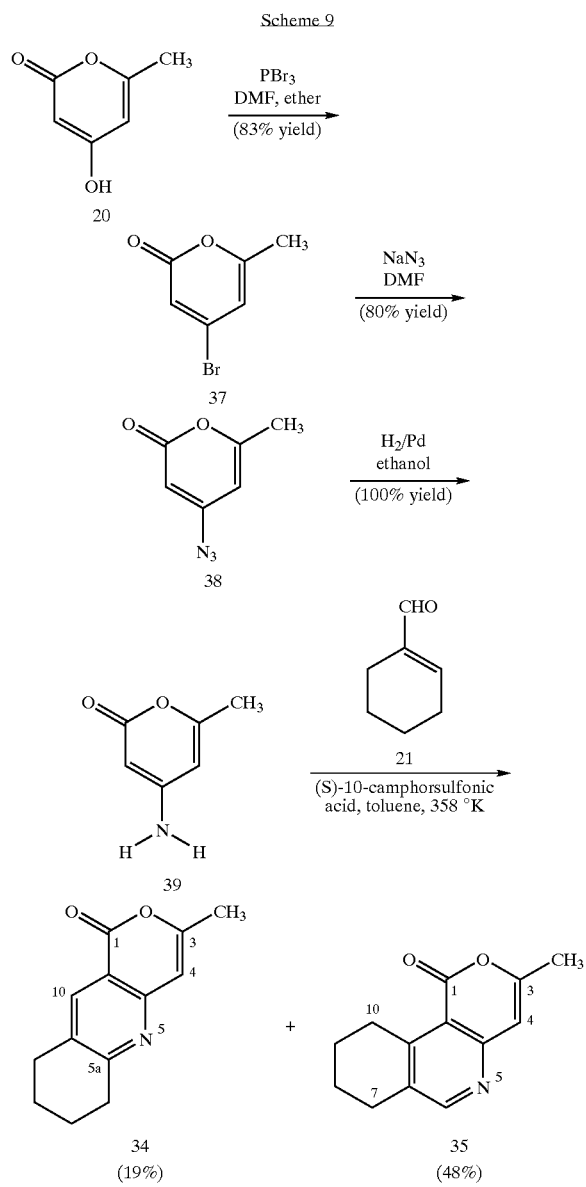

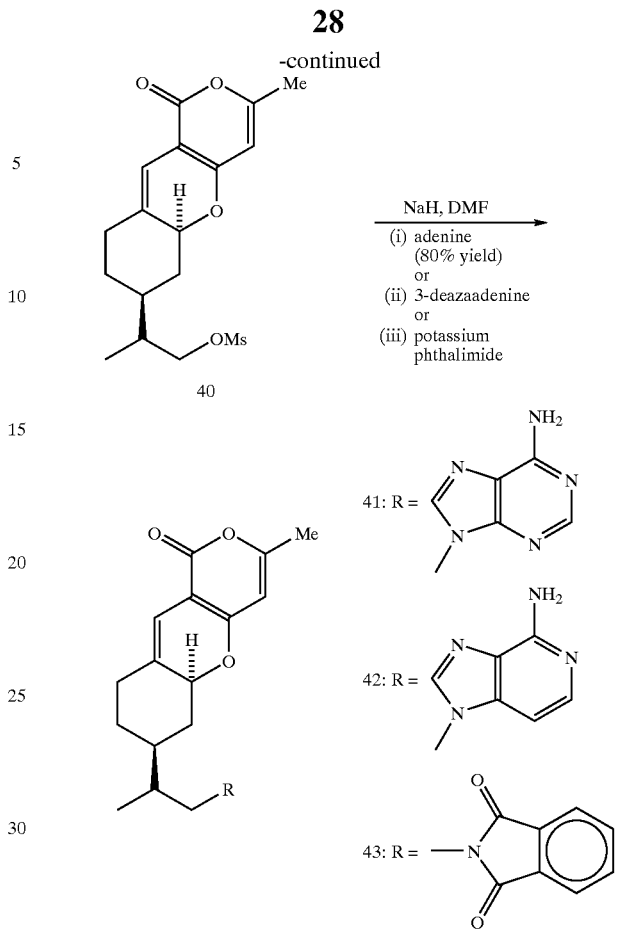

Experimental Section

General Methods. Nuclear magnetic resonance spectra were obtained at 400 MHz for $^1$H and 100 MHz $^{13}$C for in deuteriochloroform, unless otherwise indicated. Infrared spectra are reported in wavenumbers (cm$^{-1}$). Mass spectra were taken from a Hewlett Packard 5890 Series II, GC-HPLC-MS. FAB spectra were taken by using Xe beam (8 KV) and m-nitrobenzyl alcohol as matrix. Silica gel, grade 643 (200~425 mesh), was used for the flash chromatographic separation. THF and diethyl ether were distilled over sodium and benzophenone before used. Methylene chloride was distilled over CaH$_2$ and toluene and benzene were distilled over LiAlH$_4$. Ethyl acetate was dried over CaCl$_2$ and filtered and distilled under argon atmosphere.

1. 3-Methyl-1H,7H-5a,6,8,9-tetrahydro-1-oxopyrano[4,3-b][1]benzopyran (23).

A mixture of 100 mg (0.91 mmol) of 1-cyclohexenecarboxaldehyde (21), 115 mg (0.91 mmol) of 4-hydroxy-6-methyl-2-pyrone (20), and 52 mg (0.46 mmol) of L-proline in 5 mL of ethyl acetate was stirred at 70° C. under argon atmosphere for 24 h. The mixture was cooled to room temperature, diluted with 100 mL of methylene chloride, washed with saturated aqueous NaHCO$_3$ solution twice (30 mL each), with water (60 mL), and then with brine (60 mL), dried (MgSO$_4$), filtered, and concentrated to give 200 mg of crude product. Column chromatography on silica gel of the crude product using a gradient mixture of hexane and diethyl ether as eluant gave 0.150 g (76% yield; 80% based on recovered starting pyrone) of 23 and 6 mg (5% recovery) of 20. Compound 23: mp 110~112° C.; single crystal X-ray diffraction analysis was carried out on a single crystal obtained from the recrystallization from ether-hexane. IR (Nujol) υ 1710 (s, C=O), 1630 (C=C), 1560. $^1$H NMR δ 6.07 (s, 1H, C10H), 5.7 (s, 1H, C4H), 5.02 (dd, J=11, 5Hz, 1H, C5aH), 2.41 (m, 1H, C9H), 2.18 (s, 3H, Me), 2.13 (m, 1H, C5aH), 2.02~1.88 (m, 2H), 1.8~1.7 (m, 2H), 1.5~1.4 (m, 2H); $^{13}$C NMR δ 174 (s, C=O), 163.24 (s, C3), 161.38 (s, C4a), 133.06 (s, C10a), 109.17 (d, C10), 99.76 (d, C4), 97.33 (s, C9a), 79.69 (s, C5a), 35.15 (t, C9), 33.14 (t, C6), 26.89 (t, C7), 24.52 (t, C8), 20.06 (q, Me); MS (CI) m/z 219 (M+1). Analysis Calculated for $C_{13}H_{14}O_3$: C 71.54; H, 6.47. Found: C, 71.39; H, 6.53.

2. (5aS,7S)-7-Isopropenyl-3-methyl-1H,7H-5a,6,8,9-tetrahydro-1-oxopyrano[4,3-b][1]benzopyran (24).

From 1.000 g (7.93 mmol) of pyrone 20 and 1.191 g (7.93 mmol) of S-perilaldehyde (22), 1.596 g (78% yield) of 24 was obtained after column chromatographic separation: yellow solid, mp 140–141° C.; $[α]^{22}_D$=+31.9° (c 0.75, CHCl$_3$); $^1$H NMR δ 6.1 (s, 1H, C10H), 5.72 (s, 1H, C4H), 5.1 (dd, J=11 Hz, 5 Hz, 1H, C5aH), 4.75 (m, 1H, =CH), 4.73 (m, 1H, =CH), 2.48 (ddd, J=14 Hz, 4 Hz, 2.4 Hz, 1H), 2.22–2.02 (series of m, 3H), 2.19 (s 3H, C4-Me), 1.88–1.72 (series of m, 2H), 1.74 (s, 3H, MeC=), 1.31 (ddd, J=25 Hz, 12.8 Hz, 4 Hz, 1H); $^{13}$C NMR δ 163.4 (s, C=O), 162.6 (s, C3), 161.7 (s, C4a), 147.9 (s, C10a), 132.3 (s, =C), 109.8 (d, C10), 109.6 (t, =CH$_2$), 99.9 (d, C4), 97.5 (s, C9a), 79.4 (s, C5a), 43.6 (d, C7), 40.0 (t), 32.5 (t), 32.1 (t), 20.9 (q, Me), 20.3 (q, Me); MS FAB, m/z 259 (M+1, 70%), 258, 257, 215, 189, 139 (100). Anal. Calcd for $C_{16}H_{18}O_3$: C, 74.4; H, 7.02. Found: C, 74.17; H, 7.33.

3. 3-Methoxycarbonylmethyl-1H,7H-5a,6,8,9-tetrahydro-1-oxopyrano[4,3-b][1]benzopyran.

To a cold (−10° C.) solution of 0.31 mL (2.20 mmol) of diisopropylamine in 10 mL of diethyl ether under argon was added 1.40 mL (2.20 mmol; 1.6 M solution in hexanes) of n-butyllithium via syringe and the solution was stirred for 1 hour. In another flask, 0.400 g (1.83 mmol) of 23 in 10 mL THF under argon atmosphere was prepared and cooled to −78° C. The freshly prepared LDA was added to the above pyrone solution via cannula, and then, 0.32 mL (1.83 mmol) of HMPA was added via syringe. The solution was allowed to react at −78° C. for 3 hours. Finally, 0.14 mL (1.83 mmol) of methyl chloroformate was added to the resulting anion solution at −78° C., stirred at this temperature for 2 hours, then diluted with 30 mL of distilled water, and extracted with diethyl ether (50 mL×3). The combined ether was washed with brine (50 mL, dried over MgSO$_4$, concentrated, and column chromatographed on silica gel using a gradient mixture of hexane and ether as eluent to give 0.215 g (72% yield based on recovered starting material 23) of the title compound and 0.165 g (40% recovery) of 23. $^1$H NMR δ6.09 (s, 1H, C4H), 6.05 (s, 1H, C10H), 5.07 (dd, J=11.2 Hz, 5.6 Hz, 1H, C5aH), 3.80 (s, 5H, OMe and CH$_2$—CO), 2.44 (m, 1H, C9H), 2.14 (dd, J=12.0 Hz, 3.6 Hz, 1H), 2.03~1.72 (m, 4H), 1.55~1.31 (m, 2H); $^{13}$C NMR d 165.2 (s, C=O), 162.3 (s, C=O), 161.4 (s, C3), 153.8 (s, C4a), 134.7 (s, C10a), 108.9 (d, C4), 102.6 (d, C10), 99.5 (s, C9a), 80.1 (d, C5a), 56.0 (q, OMe), 53.6 (t), 35,3 (t), 33.3 (t), 26.9 (t), 24.5 (t).

4. {1H,7H-5a,6,8,9-Tetrahydro-1-oxopyrano[4,3-b][1]benzopyran-3-yl}acetic acid (1).

To a cold (−10° C.) solution of 1.67 mL (12.0 mmol) of diisopropylamine in 20 mL of diethyl ether under argon was added 7.50 mL (12.00 mmol; 1.6 M solution in hexanes) of n-butyllithium via syringe and the solution was stirred for 1 hour at this temperature. In another flask, 1.300 g (6.00 mmol) of pyrone 23 in 20 mL THF under argon atmosphere was prepared and cooled to −78° C. The freshly prepared LDA was added to the above pyrone solution via cannula. The solution was allowed to react at −78° C. for 2 hours. Carbon dioxide was then flushed through the reaction solution via a balloon of CO$_2$ while the reaction flask was inserted with a needle to release the gas. The color of the blue anion soon changed to brownish color. The reaction mixture was stirred for 30 minutes, quenched with 20 mL saturated aqueous NaHCO$_3$, and 20 mL distilled water, and extracted with diethyl ether (30 mL×3). The aqueous layer was acidified with 6 N HCl, and extracted with methylene chloride (50 mL×3). The combined methylene chloride was washed with 50 mL water, 50 mL brine, dried over MgSO$_4$, and concentrated to give 1.480 g pure product. $^1$H NMR δ 6.15 (s, 1H, C4H), 5.92 (s, 1H, C10H), 5.16 (dd, J=10.8 Hz, 4.8 Hz, 1H, C5aH), 3.53 (s, 2H, CH$_2$—CO), 2.41 (d, J=14.4, 1H), 2.10~1.96 (m, 2H), 1.83~1.63 (m, 3H), 1.46 (m, 1H), 1.29~1.23 (m, 1H); $^{13}$C NMR (DMSO-d6) δ 169.4 (s, enol =COH), 162.4 (s, C=O), 160.9 (s, C3), 158.2 (s, C4a), 134.4 (s, C10a), 108.2 (d, C10), 100.8 (d, C4), 99.3 (s, C9a), 79.1 (d, C5a), 97.2 (d, enol C=), 34.8 (t, CH$_2$), 32.4 (t, CH$_2$), 26.5 (t, CH$_2$), 23.9 (t, CH$_2$). Compound 1 was also prepared from the basic hydrolysis of 3-methoxycarbonylmethyl-1H,7H-5a,6,8,9-tetrahydro-1-oxopyrano[4,3-b][1]-benzopyran. To a solution of 0.80 g (0.29 mmol) of 3-(methoxycarbonylmethyl)-1H,7H-5a,6,8,9-tetrahydro-1-oxopyrano[4,3-b][1]-benzopyran in a solution of 4 mL of THF and water (1:3) was added 0.033 g (0.58 mmol) of KOH at room temperature. The mixture was heated to 40° C. for 14 h. It was cooled to room temperature, 30 mL of distilled water was then added, and was extracted three times with methylene chloride (40 mL each). The combined methylene chloride layer was washed with 30 mL of distilled water, and 30 mL of brine, and concentrated to give 0.021 g of starting material (26% recovery). The aqueous layer was acidified with 10 mL of 1 N HCl solution and extracted three times with methylene chloride (50 mL each). The combined organic layer was washed twice with distilled water (40 mL each), 40 mL of brine, dried over MgSO$_4$, concentrated to give 0.33 g of 1 (58% yield, based on recovered starting material).

5. {(5aS,7S)-7-Isopropenyl-1H,7H-5a,6,8,9-tetrahydro-1-oxopyrano[4,3-b][1]benzopyran-3-y}acetic acid (6).

To a cold (−10° C.) solution of 0.27 mL (1.90 mmol) of diisopropylarnine in 5 mL of diethyl ether under argon was added 1.20 mL (1.90 mmol; 1.6 M solution in hexanes) of n-butyllithium via syringe and the solution was stirred for 1 hour at this temperature. In another flask, 0.250 g (0.97 mmol) of 24 in 5 mL THF under argon atmosphere was prepared and cooled to −78° C. The freshly prepared LDA was added to the above solution via cannula. The solution was allowed to react at −78° C. for 2 hours. Carbon dioxide was then flushed into the solution through a balloon and insertion of a needle to allow the gas to flush out from the reaction mixture. The color of the blue anion soon changed to brownish color. The reaction mixture was stirred for 30 minutes, quenched with 10 mL saturated aqueous NaHCO$_3$, and 10 mL distilled water, and extracted with ether (15 mL×3). The aqueous layer was acidified with 6 N HCl and extracted with methylene chloride (30 mL×3). The combined methylene chloride was washed with 30 mL water, and 30 mL brine, dried over MgSO$_4$, and concentrated to give 0.271 g pure product. $^1$H NMR δ 6.09 (s, 1H, C4H), 5.95 (s, 1H, C10H), 5.14 (dd, J=11.2, 4.8 Hz, 1H, C5aH), 4.76 (s, =CH), 4.73 (s, =CH), 3.51 (s, 2H, CH$_2$), 2.50 (d, J=14 Hz, 1H), 2.22~2.02 (a series of m, 3H), 1.88~1.74 (m, 2H), 1.75 (s, 3H, Me), 1.31 (m, 1H). This acid was also prepared from the basic hydrolysis of benzyl ester 30.

To a 0.122 g (0.31 mmol) of benzyl ester 30 in 4 mL THF solution was added 1.5 mL of 1% NaOH aqueous solution at room temperature. The reaction mixture was stirred at room temperature for 2 hours, and acidified with 0.1 mL of 4 N HCl in dioxane. The solvent was removed via vacuum, the residue was then dissolved in 20 mL methylene chloride and filtered. The filtrate was then concentrated and column chromatographed to give 0.093 g of 6 (100% yield).

6. 2-{1H,7H-5a,6,8,9-Tetrahydro-1-oxopyrano[4,3-b][1]benzopyran-7-yl}-propanal (33).

A solution of 0.070 g (0.25 mmol) of 32 and 0.160 g (0.38 mmol) of Dess Martin periodinane in 4 mL of methylene chloride was stirred at room temperature for 48 hours. The reaction mixture was filtered through Celite, and the filter cake was washed with 50 mL methylene chloride. The organic layer was concentrated and column chromatographed on silica gel using a gradient mixture of hexane and ether as eluent to give 0.060 g of 33 (87% yield). $^1$H NMR δ 9.67 (d, J=0.4 Hz, 1H, CHO), 6.09 (s, 1H, C10H), 5.71 (s, 1H, C4H), 5.10 m, 1H, C5aH), 2.50~2.46 (m, 1H), 2.36~2.31 (m, 1H), 2.19 (s, 3H, Me), 2.17~2.01 (m, 2H), 1.79~1.57 (m, 3H), 1.30~1.17 (m, 1H), 1.11 (d, J=7.2 Hz, 3H, Me); $^{13}$C NMR d 204.1 (d, CHO), 163.3 (s, C=O), 162.5 (s, C3), 161.8 (s, C4a), 131.7 (s, C10a), 109.8 (d, C4), 99.8 (d, C10), 97.4 (s, C9a), 79.0 (d, C5a), 50.7 (d), 39.2 (d), 37.3 (t), 36.3 (t), 32.1 (t), 20.2 (q, Me), 10.1 (q, Me).

7. n-Butyl 2-hydroxy-3-{1H,7H-5a,6,8,9-tetrahydro-1-oxopyrano[4,3-b][1]benzopyran-3-yl}-propanoate (25).

To a cold (−10° C.) solution of 0.13 mL (0.92 mmol) of diisopropylamine in 5 mL of diethyl ether under argon was added 0.56 mL (0.92 mmol; 1.6 M solution in hexanes) of n-butyllithiun via syringe, and the solution was stirred for 1 hour. In another flask, a solution of 0.100 g (0.46 mmol) of 23 in 5 mL of THF under argon was cooled to −78° C. The freshly prepared LDA solution was added to the above solution at −78° C. via cannula, then, 0.08 mL (0.46 mmol) of HMPA was added to the reaction mixture via syringe and stirred at −78° C. for 3 hours. To the reaction solution, a solution of 0.060 g (0.46 mmol) of n-butyl glyoxalate in 3 mL THF was subsequently added to the anion solution at −78° C. via cannula, and stirred for 1 hour at this temperature. The solution was diluted with 20 mL of distilled water, and extracted three times with ethyl ether (50 mL each). The combined organic layer was washed with 30 mL of distilled water, 30 mL of brine, dried over MgSO$_4$, concentrated, and column chromatographed over silica gel to give 0.132 g of 1.112 (86% yield). $^1$H NMR δ 6.03 (s, 1H, C10H), 5.87 (s, 1H, C4 H), 5.03 (m, 1H, C5a), 4.53 (t, J=4 Hz, 1H, CH—OH), 4.22~4.18 (m, 2H, OCH$_2$), 2.94 (d, J=14.8 Hz, 1H, CH$_2$CHOH), 2.75 (dd, J=14.8 Hz, 8 Hz, 1H, CH$_2$CHOH), 2.41 (d, J=14 Hz, 1H), 2.12 (d, J=8 Hz, 1H), 2.02~1.28 (m, 12H), 0.94 (t, J=7.2 Hz, 3H, Me); $^{13}$C NMR δ 173.5 (s, C=O), 162.9 (s, C1), 162.2 (s, C3), 159.7 (C4a), 133.6 (s, C10a), 109.0 (d, C4), 101.7 (d, C10), 98.2 (s, C9a), 79.7 (d, C5a), 67.9 (t, CHOH), 65.9 (d, CH$_2$O), (38.8 (t), 35.2 (t), 33.2 (t), 30.5 (t), 26.9(t), 24.5 (t), 19.0 (t), 13.6 (q, Me).

8. 2-Hydroxy-3-{1H,7H-5a,6,8,9-tetrahydro-1-oxopyrano[4,3-b][1]benzopyran-3-yl}-propanoic acid (3).

To 0.030 g (0.09 mmol) of 25 in 2 mL THF was added 0.5 mL of 1% aqueous NaOH solution at room temperature. The reaction mixture was stirred for 1 hour, diluted with 20 mL of distilled water, acidified with a few drops of 1 N HCl solution, extracted three times with methylene chloride (40 mL each). The combined organic layer was washed with 20 mL brine, dried over MgSO$_4$, concentrated to give 0.018 g of 3 (72% yield). $^1$H NMR δ 6.01 (s, 1H, C10H), 5.92 (s, 1H, C4H), 5.05 (dd, J=11.2 Hz, 4.8 Hz, 1H, C5a H), 4.58 (dd, J=7.2 Hz, 4 Hz, 1H, CH—OH), 3.02 (dd, J=14.8 Hz, 4 Hz, 1H, CH$_2$—CHOH), 2.85 (dd, J=14.8 Hz, 7.2 Hz, 1H, CH$_2$—CHOH), 2.41 (d, J=14 Hz, 1H), 2.13 (m, 1H), 2.01~1.70 (m, 4H), 1.48~1.22 (m, 2H).

9. n-Butyl 2-Hydroxy-3-{1H,7H-5a,6,8,9,10,11-hexahydro-10-hydroxy-1-oxopyrano[4,3-b][1]benzopyran-3-yl}-propanoate (25A).

A solution of 0.100 g (0.29 mmol) of 1.112 and 0.57 mL (0.57 mmol) of BH$_3$.THF (1.0 M in THF) in 5 mL THF was stirred under argon at 0° C. for 2 hours. The reaction solution was warmed to room temperature and stirred for overnight. Subsequently, 2 mL of 1% aqueous of NaOH and 3 mL of 30% hydrogen peroxide was added, stirred at room temperature for 4 hours, diluted with 30 mL of distilled water, and extracted four times with methylene chloride (40 mL each). The combined organic layer was washed with 20 mL brine, dried over MgSO$_4$, and concentrated to give 0.033 g of 25A (32% yield). Compound 25A: $^1$H NMR δ 5.97 (s, 1H, C4H), 4.54 (s, 1H, C5a), 4.42 (s, 1H, C10H), 4.37 (s, 1H, CH—OH), 2.99 (dd, J=10.8 Hz, 4 Hz, 1H, CH$_2$—CHOH), 2.76 (dd, J=8.4 Hz, 6.4 Hz, 1H, CH$_2$—CHOH), 2.17~1.22 (m, 14H), 0.95 (t, J=7.2 Hz, 3H, Me).

10. 2-Hydroxy-3-{1H,7H-5a,6,8,9,10,11-hexahydro-10-hydroxy-1-oxopyrano[4,3-b][1]benzopyran-3-yl}-propanoic acid (2).

A solution of 0.026 g (0.07 mmol) of 25A and 1.5 mL of 1% aqueous NaOH solution in 2 mL THF was stirred at room temperature for 1 hour. The reaction mixture was then acidified with a few drops of 1 N HCl solution. The solvent was removed using rotary evaporator. The residue was dissolved in 10 mL of ethanol, and filtered through a 1 inch long of silica gel packed in a pipette column. The filtrate was concentrated to give 0.016 g of 2 (73% yield). 1H NMR δ 6.19 (s, 1H, C4H), 4.63 (dd, J=7.6 Hz, 4.8 Hz, 1H, C5aH), 4.46 (m, 1H, CH—OH), 3.07 (dd, J=15.2 Hz, 4 Hz, 1H), 2.93 (m, 2H), 2.24~1.25 (m, 8H).

11. n-Butyl 2-(Methanesulfonyloxy)-3-{1H,7H-5a,6,8,9-tetrahydro-1-oxopyrano[4,3-b][1]benzopyran-3yl}-propanoate (25B).

A solution of 0.200 g (0.29 mmol) of 25, 0.24 mL (0.87 mmol) of triethylamine, and 0.06 mL (0.87 mmol) of methanesulfonyl chloride in 5 mL methylene chloride was stirred at 0° C. for 1 hour, and at room temperature for 2 hours. The reaction mixture was diluted with 30 mL of saturated aqueous NaHCO$_3$, and extracted three times with methylene chloride (30 mL each). The combined organic layer was washed with 30 mL of distilled water, 30 mL brine, dried over MgSO$_4$, concentrated, and purified through silica gel column chromatography to give 0.193 g of 25B (90% yield, based on recovered starting material 25) and 0.240 g of 25 (13% recovery). Compound 1.116: $^1$H NMR δ 6.01 (s, 1H, C4H), 5.88 (s, 1H, C10H), 5.31 (dd, J=8.4 Hz, 4.4 Hz, 1H, CH—OMs), 5.07 (d, J=8 Hz, 1H, C5a), 4.26~4.21 (m, 2H, OCH$_2$), 3.12 (s, 3H, Me), 3.09~2.96 (m, 2H, CH$_2$—COMs), 2.42 (d, J=14.0 Hz, 1H), 2.16~1.28 (m, 11H), 0.94 (t, J=7.2 Hz, 3H, Me); $^{13}$C NMR δ 167.6 (s, C=O), 162.4 (s, C1), 161.4 (s, C3), 156.9 (s, C4a), 134.2 (s, C10a), 108.7 (d, C4), 102.2 (s, C9a), 98.5 (d, C10), 79.8 (d, C5a), 74.3 (d, CH—OMs), 66.3 (t, OCH2), 38.8 (t), 36.3 (t), 35.1 (t), 35.0 (t, stereoisomer), 33.1 (t), 31.6 (t, stereoisomer), 30.2 (t), 26.7(t), 24.3 (t), 18.9 (q), 13.5(q, Me).

12. n-Butyl 3-{1H,7H-5a,6,8,9-tetrahydro-1-oxopyrano[4,3-b][1]benzopyran-3-yl}-acrylate (28).

The solution of 0.072 g (0.17 mmol) of 25B and 0.07 mL (0.50 mmol) of DBU in 5 mL of toluene under argon was stirred at room temperature for 10 minutes. The reaction mixture was diluted with 30 mL of distilled water, and extracted three times with diethyl ether (50 mL each). The combined ether layer was washed with 30 mL of brine, dried over MgSO$_4$, and concentrated to give 0.054 g of 28 (100% yield). Compound 28: $^1$H NMR δ 7.04 (d, J=15.6 Hz, 1H, CH=), 6.66 (d, J=15.6 Hz, 1H, =CH), 6.11 (s, 1H, C4H), 6.06 (s, 1H, C10H), 5.09 (dd, J=11.2 Hz, 4.8 Hz, 1H, C5aH), 4.19 (t, J=6.8 Hz, 2H, OCH$_2$), 2.45 (d, J=14 Hz, 1H), 2.18~1.25 (m, 11H), 0.94 (t, J=4.8 Hz, 3H, Me); $^{13}$C NMR δ 166.2 (s, C=O), 161.6 (s, C1), 160.8 (s, C3), 154.8 (d, CH=), 136.1 (s, C4a), 123.7 (d, =CH), 109.5 (d, C4), 105.7 (d, C10), 102.2 (s, C9a), 80.2 (d, C5a), 65.0 (t, OCH$_2$), 35.4 (t), 33.5 (t), 30.8 (t), 27.0 (t), 24.6 (t), 19.3(t), 13.8 (q, Me).

13. 3-{1H,7H-5a,6,8,9-Tetrahydro-1-oxopyrano[4,3-b][1]benzopyran-3-yl}-propenoic acid (5).

A solution of 0.014 g (0.04 mmol) of 28 and 1 mL of 1% aqueous NaOH solution in 2 mL of THF at room temperature was stirred at room temperature for 12 h. The reaction mixture was subsequently acidified with a few drops of 1 N HCl, diluted with 15 mL of distilled water, and extracted three times with methylene chloride (30 mL each). The combined organic layer was washed with 20 mL of brine, dried over MgSO$_4$, concentrated, and purified through silica gel column chromatography to give 0.120 g of 5 (100% yield). Compound 5: $^1$H NMR δ 7.19 (d, J=15.6 Hz, 1H, CH), 6.48 (d, J=15.6 Hz, 1H =CH), 6.45 (s, 1H, C4H), 6.02 (s, 1H, C10H), 5.20 (dd, J=11.2 Hz, 4.8 Hz, 1H, C5aH), 2.12~1.28 (m, 8H).

14. n-Butyl 3-(N-Methylamino)-3-{1H,7H-5a,6,8,9-tetrahydro-1-oxopyrano[4,3-b][1]benzopyran-3-yl}-propanoate (28A).

A solution of 0.050 g (0.15 mmol) of 28 and 0.047 g (1.5 mmol) of methylamine in 2 mL of THF was stirred at 0° C. for 4 hours. The reaction mixture was then stirred at room temperature for 2 hours. The solvent was removed through rotary evaporation. The residue was purified through silica gel column chromatography to give 0.011 g of 28A (63% yield, based on recovered starting material 28), and 0.034 g of 28 (68% recovery). Compound 28A: $^1$H NMR δ 6.06 (s, 1H, C10H), 5.78 (s, 1H, C4H), 5.04 (d, J=5.2 Hz, 1H, C5aH), 4.14 (t, J=6.4 Hz, 2H, OCH$_2$), 3.59 (t, J=6.4 Hz, 1H, CH—N), 2.8 (s, 3H, MeN), 2.79~2.67 (m, 2H), 2.15~1.31 (m, 12H), 0.93 (t, J=7.6 Hz, 3H, Me).

15. 3-(N-Methylamino)-3-{1H,7H-5a,6,8,9-tetrahydro-1-oxopyrano[4,3-b][1]benzopyran-3yl}-propanoic acid (29).

A solution of 0.013 g (0.04 mmol) of 28A and 1 mL of 1% aqueous NaOH solution in 2 mL THF was stirred at room temperature for 2 hours and neutralized with HCl. The solvents were then removed through rotary evaporation to give 0.006 g of 29 (55% yield). Compound 29: $^1$H NMR δ 6.17 (s, 1H, C4H), 5.95 (s, 1H, C10H), 5.22 (m, 1H, C5a H), 3.95 (m, 1H, CH—N), 3.20~3.17 (m, 2H), 2.80 (s, 3H, Me-N), 2.50~1.26 (m, 8H).

16. (5aS,7s)-3-(Benzyloxycarbonyl)methyl-7-isopropenyl-1H,7H-5a,6,8,9-tetrahydro 1-oxopyrano[4,3-b][1]benzopyran (30)

To a cold (−10° C.) solution of 0.43 mL (3.10 mmol) of diisopropylamine in 20 mL of diethyl ether under argon was added 3.00 mL (3.10 mmol; 1.6 M solution in hexanes) of n-Butyl Lithium via syringe and the solution was stirred for 1 hour. In another flask, 0.400 g (1.55 mmol) of 24 in 20 mL of THF under argon was cooled to −78° C. The freshly prepared LDA solution was added to the above solution at −78° C. via cannula, then, HMPA was added to the reaction mixture via syringe and stirred at −78° C. for 3 hours. To the reaction solution, 0.44 mL (3.1 mmol) of benzyl chloroformate in 20 mL THF was subsequently added to the anion solution at −78° C. via cannula, and stirred for 2 more hours at this temperature. The reaction was diluted with 40 mL of distilled water and extracted three times with methylene chloride (40 mL each). The combined organic layer was washed with 40 mL of brine, dried over MgSO$_4$, concentrated, and column chromatographed through silica gel using a gradient mixture of hexane and ether to give 140 g of 30 (95% yield based on recovered starting material 24) and 0.308 g (77% recovery) of 24. $^1$H NMR δ 7.38~7.31 (m, 5H, Ar), 6.08 (s, 1H, C4H), 5.91 (s, 1H, C10H), 5.28 (s, 2H, CH$_2$OC=O), 5.12 (dd, J=5.2 Hz, 1.2 Hz, 1H, C5aH), 4.75 (s, 1H, =CH$_2$), 4.72 (s, 1H, =CH$_2$), 3.50 (s, 2H, CH$_2$C=O), 2.49~2.45 (m, 1H), 2.21~2.01 (m, 3H), 1.86~1.70 (m, 2H), 1.73 (s, 3H, Me), 1.34~1.25 (m, 1H); $^{13}$C NMR δ 167.5 (s, C=O of ester), 162.6 (s, C=O), 161.9 (s, C3), 156.2 (s, C4a), 147.8 (s, C10a), 135.2 (s, Ar), 133.2 (s, C=), 128.7 (d, Ar), 128,6 (d, Ar), 128.4 (d, Ar), 109.8 (d, C10), 109.3 (t, =CH$_2$), 102.2 (d, C4), 98.8 (s, C9a), 79.5 (d, C5a), 67.5 (t, OCH$_2$Ar), 43.4 (t, CH$_2$), 39.9 (d, CH), 39.4 (t, CH$_2$), 32.4 (t, CH$_2$), 31.9 (t, CH$_2$), 20.8 (q, Me).

17. (5aS,7S)-3-(Benzyloxycarbonyl)methyl-7-(2-hydroxy-1-methyl)ethyl-1H,7H-5a,6,8,9-tetrahydro-1-oxopyrano[4,3-b][1]benzopyran (31)

A solution of 0.115 g (0.29 mmol) of 30 and 0.15 mL (0.15 mmol) of BH$_3$.THF complex (1.0 M in THF) in 5 mL THF was stirred for 1 h and then stored at −25° C. for overnight. The reaction mixture was allowed to warm up to 0° C., then, 2 mL of 0.5% NaOH aqueous solution and 2 mL of 30% hydrogen peroxide solution were added to the reaction mixture at 0° C., and stirred for 6 hours. The reaction mixture was then neutralized with a few drops of 6 N HCl, diluted with 30 mL of distilled water, and extracted three times with methylene chloride (30 mL each). The combined methylene chloride was washed with 30 mL brine, dried over MgSO$_4$, concentrated, separated through silica gel column chromatography to give 0.061 g of 31 (69% yield based on recovered starting material 30) and 0.030 g of 30 (26% recovery). $^1$H NMR dδ7.39~7.31 (m, 5H, Ar), 6.06 (s, 1H, C10H), 5.91 (s, 1H, C4H), 5.17 (s, 2H, OCH$_2$Ar), 5.10 (dd, J=10.8 Hz, 5.6 Hz, 1H, C5aH), 3.61~3.52 (m, 2H, CH$_2$OH), 3.50 (s, 2H, CH$_2$C=O), 2.46 (dd, J=14.0 Hz, 1.2 Hz, 1H), 2.13~1.96 (m, 2H), 1.73~1.11 (m, 5H), 0.91 (d, J=2 Hz, 3H, Me); $^{13}$C NMR δ 167.6 (s, C=O), 162.7 (s, C=O), 162.1 (s, C3), 156.2 (s, C4a), 135.2 (C10a), 133.8 (s, Ar), 128.8 (d, Ar), 128.6 (d, Ar), 128.5 (d, Ar), 109.0 (d, C10), 102.3 (d, C4), 98.9 (s, C9a), 79.9 (s, C5a), 67.6 (t, OCH$_2$Ar), 40.1 (t, CH$_2$), 39.5 (t), 37.3 (t), 32.5(t), 31.2 (t) 30.5 (t), 28.7 (t), 13.3 (q, Me).

18. (5aS,7S)-7-(1-Hydroxymethyl-1-ethyl)-3-methyl-1H,7H-5a,6,8,9-tetrahydro-1-oxopyrano[4,3-b][1]benzopyran (32)

To a cold solution (−25° C.) of 0.500 g (1.94 mmol) of 24 in 10 mL THF under argon was added 1.94 mL (1.94 mmol) of BH$_3$.THF complex (1.0 M in THF). The reaction mixture was stirred at −25° C. for overnight. To it, 4 mL of 0.5% NaOH aqueous solution and 4 mL of 30% hydrogen peroxide solution were added to the reaction mixture at 0° C., and stirred for 4 hours. The reaction mixture was then diluted with 50 mL of distilled water and extracted three times with methylene chloride (50 mL each). The combined methylene chloride was washed with 40 mL of brine, dried over MgSO$_4$, concentrated, and column chromatographed on silica gel to give 0.326 g of 32 (82% yield, based on 26% recovered starting material 24) and 0.130 g of 24 (26% recovery). $^1$H NMR, δ 6.08 (s, 1H, C10H), 5.71 (s, 1H, C4H), 5.07 (t, J=5.2 Hz, 1H, C5aH), 3.62~3.52 (m, 2H, CH$_2$OH), 2.46 (m, 1H), 2.19 (s, 3H, Me), 2.13~1.99 (m, 2H), 1.73~1.51 (m, 3H), 1.19~1.12 (m, 2H), 0.92 (d, J=1 Hz, 3H, Me).

19. 4-Bromo-6-methyl-2H-pyrone (37)

To a 10 mL DMF solution at 0° C. was added dropwise a solution of 8.734 g (32 mmol) PBr₃ in 18 mL of distilled diethyl ether. Then, 1.009 g (8.0 mmol) pyrone solution in 8 mL DMF was transferred to the PBr₃ solution via cannula. The resulting mixture was heated to 60° C. for overnight. The reaction mixture was subsequently cooled to 0° C., then quenched with 40 mL of distilled water, extracted with 20 mL×6 of ethyl ether, combined ethyl layer was washed with 50 mL of distilled water, dried over MgSO₄, and concentrated to give 1.251 g of 37 (83% yield). $^1$H NMR δ 6.47 (s, C3), 6.20 (s, C5), 2.25 (s, Me); 13C NMR d 161.9 (s, C2), 159.5 (s, C6), 140.5 (s, C4), 113.7 (d, C3), 107.6 (s, C5).

20. 4-Azido-6-methyl-2H-pyrone (38)

A mixture of 1.250 g (6.61 mmol) of 1.85 and 0.645 g (9.92 mmol) of sodium azide in 25 mL DMF was stirred for 1 hour under argon atmosphere. The reaction mixture was then poured into 65 mL of ice water, stirred for 10 minutes, extracted with diethyl ether (50 mL×6), the combined ether layer was washed with 50 mL×3 of distilled water, dried over sodium sulfate, and concentrated to give 0.788 g of 38 (80% yield). $^1$H NMR δ 5.76 (d, J=2 Hz, 1H, C3H), 5.64 (dd, J=2 Hz, 0.4 Hz, 1H, C5H), 2.18 (d, J=0.4 Hz, Me); $^{13}$C NMR δ 163.7 (s, C2), 162.3 (s, C6), 156.2 (s, C4), 98.9 (d), 96.7 (d), 19.8 (q, Me).

21. 4-Amino4-methyl-2H-pyrone (39)

To a 0.310 g (2.05 mmol) of 38 and 0.031 g of 10% Pd/C in 10 mL of ethanol was maintained under 1 atm (a ballonn) of hydrogen gas for 1 hour. The reaction mixture was then filtered through Celite, and ethanol of the filtrate was removed through rotary evaporation to give 0.260 g of 39 (100% yield). $^1$H NMR δ 5.56 (s, 1H, C3H), 5.12 (s, 1H, C5 H), 4.45 (s, 2H, NH₂), 2.20 (s, Me); $^{13}$C NMR δ 163.6 (s, C2), 161.3 (s), 98.6 (d, C5), 80.4 (d, C3), 19.5 (q, Me).

22. 3-Methyl-1H-6,7,8,9-tetrahydro-1-oxopyrano[4,3-b]quinoline (34) and 3-Methyl-1H-7,8,9,10-tetrahydro-1-oxopyrano[4,3-c]iosquinoline (35)

A mixture of 0.250 g (2.28 mmol) of 1-cyclohexenecarboxaldehyde (21), 0.190 g (1.52 mmol) of 4-amino-6-methyl-2-pyrone (36), and 0.035 g (0.15 mmol) of (S)-(+)-10-camphorsulfonic acid in 12 mL of toluene was heated at 85° C. under argon atmosphere for 3 days. The mixture was cooled to room temperature, filtered, and washed with 20 mL of ethyl acetate. The filtrate was diluted with 100 mL of methylene chloride, washed with 50 mL of water, and 50 mL of brine, dried over MgSO₄, concentrated, and column chromatographed on silica gel using ethyl acetate:hexane (2.1) as eluent to give 13.3 mg of 34. (19% yield based on recovered starting material), 33 mg (48% yield based on recovered starting material) of 35 and 150 mg (79% recovery) of pyrone 36.

Compound 34: white solid, mp 71~72° C.; $^1$H NMR (CDCl₃) δ 8.15 (s, 1H, C10H), 6.44 (s, 1H, C4H), 3.01 (t, J=7 Hz, 2H, CH₂), 2.88 (t, J=7 Hz, 2H, CH₂), 2.31(s, 3H, Me), 1.95 (m, 2H, CH₂), 1.86 (m, 2H, CH₂); $^{13}$C NMR (CDCl₃) δ 168 (s, C1), 165.71 (s), 157.69 (s), 152,22 (s, C3), 137.2 (d, C10), 132.34 (s), 114.0 (s), 105.48 (d), 33.34 (t, CH₂), 28.69 (t, CH₂), 22.59 (t, CH₂), 22.32 (t, CH₂), 19.89 (q, Me); MS FAB 216 (M+1).

Compound 35: white solid, mp 73~74° C.; $^1$H NMR (CDCl₃) δ 8.50 (s, 1H, C6H), 6.43 (s, 1H, C4H), 3.35 (t, J=6 Hz, 2H, CH₂), 2.82 (t, J=6 Hz, 2H, CH₂), 2.29(s, 3H, Me), 1.90–1.80 (m, 4H, CH₂); $^{13}$C NMR (CDCl₃) δ 162.5 (s, C1), 157.4 (s), 156.4 (s), 154.4 (s), 151.4 (s), 132.7 (s), 114.6 (s), 106.5 (d, C4), 28.6 (t, CH₂), 27.6 (t, CH₂), 22.6 (t, CH₂), 21.7 (t, CH₂), 19.9 (q, Me); MS FAB 216 (M+1), 215, 188, 154, 136.

23. (5aS,7S)-7-{[1(1-Methylsulfonyloxy)methyl]ethyl}-3-methyl-1H,7H-5a,6,8,9-tetrahydro-1-oxopyrano[4,3-b][1]benzopyran (40).

To a solution of 0.500 g (0.18 mmol) of 32 in 5 mL methylene chloride under argon was added 0.08 mL (0.54 mmol) of triethylamine and 0.02 mL (0.27 mmol) of methanesulfonyl chloride at 0° C. The resulting mixture was stirred at this temperature for 3 hours, diluted with 30 mL of distilled water, and extracted three times with methylene chloride (30 mL each). The combined methylene chloride was washed with 20 mL of saturated aqueous sodium bicarbonate, 20 mL brine, dried over MgSO₄, concentrated, and column chromatographed to give 0.060 g of 40 (94% yield). $^1$H NMR δ 6.08 (s, 1H, C10H), 5.71 (s, 1H, C4H), 5.06 (m, 1H, C5aH), 4.18~4.08 (m, 2H, CH₂O), 3.03 (s, 3H, MeS), 2.49 (d, J=2.8 Hz, 1H), 2.19 (s, 3H, Me), 2.14~1.11 (m, 7H), 0.98 (d, J=6.8 Hz, 3H, Me); $^{13}$C NMR (contains stercoisomer at C1') δ 161.8 (s, C═O), 132.4, 109.6, 105.2, 99.8, 79.2, 72.3, 38.9, 37.5, 37.2, 36.9, 32.2, 30.8, 28.6, 20.2, 13.3, 13.2.

24. (5aS,7S)-7-[1-(9-Adenylmethyl)-ethyl]-3-methyl-1H,7H-5a,6,8,9-tetrahydro-1-oxopyrano[4,3-b][1]benzopyran (41).

To a solution of 0.022 g (0.47 mmol) of NaH in 3 mL DMF was added 0.046 g (0.34 mmol) of adenine. The reaction mixture was allowed at room temperature for 2 hours. The above anion was then added to 0.110 g (0.3 mmol) of 40 in 3 mL DMF. The reaction mixture was stirred 70° C. for overnight. After the reaction was cooled to r.t., DMF was removed via vacuum. The residue was subjected to silica gel column chromatography using mixture of methylene chloride and methanol as eluent to obtain 0.100 g of 41 (85% yield).

25. (5aS,7S)-7-{1-[9-(3-Deazaadenyl)methyl]-ethyl}-3-methyl-1H,7H-5a,6,8,9-tetrahydro-1-oxopyrano[4,3-b][1]benzopyran (42).

To a solution of 0.005 g (0.47 mmol) of NaH in 2 mL DMF under argon was added 0.019 g (0.14 mmol) of 3-deazaadenine at room temperature. The reaction was stirred at room temperature for 2 hours. The above anion solution was then added to 0.050 g (0.14 mmol) of 40 in 1 mL DMF. The reaction mixture was then stirred at 70° C. for overnight. The solvent was removed via vacuum and the residue was subjected to silica gel column chromatography using mixture of methylene chloride and methanol as eluent to obtain 0.044 g of 42 (80% yield).

26. (5aS,7S)-7-[(1-Azidomethyl)-ethyl]-3-methyl-1H,7H-5a,6,8,9-tetrahydro-1-oxopyrano[4,3-b][1]benzopyran (43).

To a solution of 0.120 g (0.34 mmol) of 40 in 5 mL under argon was added 0.088 g (1.36 mmol) of sodium azide at room temperature. The reaction mixture was then stirred at 70° C. for overnight, cooled to room temperature, diluted with 20 mL of distilled water, and extracted three times with methylene chloride (30 mL each). The combined methylene chloride was washed with 20 mL brine, dried over MgSO₄, concentrated, and purified through silica gel column chromatography using mixture of hexane and ether as eluent to give 0.071 g of 43 (70% yield). $^1$H NMR δ 6.07 (s, 1H, C10H), 5.72 (s, 1H, C4H), 5.06 (m, 1H, C5aH), 3.32~3.20 (m, 2H, CH₂N₃), 2.49~2.44 (m, 1H), 2.19 (s, 3H, Me), 2.10~1.99 (m, 2H), 1.74~1.51 (m, 3H), 1.26~1.22 (m, 2H), 0.95 (d, J=6.8 Hz, 3H, Me); $^{13}$C NMR δ 163.3 (s, C═O), 163.3 (s), 162.5 (s), 132.3 (s), 109.4 (d), 99.8 (d), 97.4 (s), 79.4 (d, C5a), 55.4 (t, CH₂N₃), 39.0 (d), 38.0 (d), 37.6 (t), 36.8 (t), 32.2(t), 30.8 (t), 28.5 (q), 20 2 (q, Me).

27. (5aS,7S)-7-[1-(N-Phthalimidylmethyl)-ethyl]-3-methyl-1H,7H-5a,6,8,9-tetrahydro-1-oxopyrano[4,3-b][1]benzopyran (44).

To a solution of 0.120 g (0.34 mmol) of 40 in 5 mL under argon was added 0.126 g (0.68 mmol) of potassium phthalimide at room temperature. The reaction mixture was stirred at 70° C. for overnight, cooled down to room temperature, diluted with 20 mL of distilled water, and extracted three times with methylene chloride (30 mL each). The combined methylene chloride was washed with 20 mL brine, dried over $MgSO_4$, concentrated, and purified through silica gel column chromatography using a gradient mixture of hexane and ether as eluent to give 0.136 g of 44 (99% yield). $^1$H NMR δ 7.89~7.72 (m, 4H, Ar), 6.08 (s, 1H, C10H), 5.72 (s, 1H, C4H), 5.04 (m, 1H, C5aH), 3.69~3.53 (m, 2H, $CH_2$—N), 2.48 (t, J=15.6 Hz, 1H), 2.08 (s, 3H, Me), 2.12~1.92 (m, 2H), 1.76~1.54 (m, 3H), 1.34~1.18 (m, 2H), 0.90 (d, J=6.8 Hz, 3H, Me); $^{13}$C NMR δ 168.8 (s, C=O), 163.4 (s, C=O), 163.3 (s, C3), 161.6 (s, C4a), 134.2 (d, Ar), 132.5 (s, C10a), 132.1 (s, Ar), 109.5 (d, C4), 99.9 (d, C10), 97.5 (s, C9a), 79.6 (d, C5a), 42.0 (t, $CH_2N$), 38.4 (d), 36.9 (d), 32.4 (t), 31.1 (t), 30 5 (t), 27.8 (q), 20 2 (q, Me)

38. 3-(Hydroxymethyl)-1H,7H-5a,6,8,9-tetrahydro-1-oxopyrano[4,3-b][1]benzopyran (26).

To a cold (−10° C.) solution of 0.3 mL (2 mmol) of diisopropylamine in 5 mL of diethyl ether under argon was added 2.6 mL (2 mmol; 1.6 M solution in hexanes) of n-butyllithium via syringe and the solution was stirred for 1 hour at this temperature. In another flask, 0.222 g (1 mmol) of 23 in 9 mL THF under argon atmosphere was prepared and cooled to −78° C. The freshly prepared LDA was added to the above solution via cannula. The solution was allowed to react at −78° C. for 3 hours. In a separated flask, 1.3125 g of $MoO_5$.HMPA.pyridine (3 mmol) was added, vacuum dried, dissolved in 10 mL of THF, and cooled to −40' C. The above anion solution was cannulated into the MoOPH solution. After the reaction was stirred for 1.5 h, 2 mL of HCl (4 M in dioxane) and 40 mL of saturated aqueous $Na_2SO_3$ were added, and the mixture was extracted four times with ethyl acetate (80 mL each). The combined organic layer was washed with 10 mL of 1 N HCl, dried over $MgSO_4$, concentrated, and column chromatographed on silica gel using a gradient mixture of hexane and ethyl acetate as eluant to give 35.2 mg (20.7% yield) of alcohol 26 and 63.4 mg (29% recovery) of 23. $^1$H NMR δ 6.03 (bs, 2H, C4&10 Hs), 5.02 (m, 1H, C5aH), 4.38 (s, 2H, $CH_2OH$), 2.42~1.2 (a series of m, 8H); $^{13}$C NMR δ 163.4 (s, C=O), 136 (s), 134.1 (s), 128.4 (s), 125.7 (d), 109.1 (d), 98.8 (s), 80 (d), 61.3 (t), 35.3 (t), 33.3 (t), 27.0 (t), 24.6 (t).

39. 3-(Formyl)-1H,7H-5a,6,8,9-tetrahydro-1-oxopyrano[4,3-b][1]benzopyran (27).

To a solution of 33.4 mg (0.142 mmol) of alcohol 26 in 6 mL of methylene chloride under argon was added 0.1093 g (0.26 mmol) of Dess-Martin periodinane. The reaction mixture was stirred at room temperature for 45 h, filtered through Celite, rinsed with 50 mL of methylene chloride, and the filtrate was concentrated to dryness to give 38.5 mg. This residue was column chromatographed on sililca gel using a gradient mixture of hexane and ether as eluant to give 16 mg (53.3% yield) of aldehyde 27 and 3.1 mg of recovered 26. $^1$H NMR δ 9.47 (s, 1H, CHO), 6.64 (s, 1H, C4H), 6.14 (s, 1, C10H), 5.16 (m, 1H, C5aH), 2.5~1.2 (a series of m, 8H); $^{13}$C NMR δ 182.52 (s, CHO), 160.1 (s, C1), 138.4 (s), 130.9 (s), 128.8 (s), 125.5 (s), 109.2 (d), 107.7 (d), 35.2 (t), 33.4 (t), 26.8 (t), 24.4 (t).

Although the description above contains many specificities, these should not be construed to limit the scope of the invention, but as merely providing illustrations of some of the presently-preferred embodiments of this invention. For example, particular selection of effective dosages is well known in the art without undue experimentation. Also, the particular selection of compounds that have the desired effect is well known to one with ordinary skill in the art. Thus, the scope of the invention should be determined by the appended claims and their legal equivalents, rather than by the examples given. All references cited herein are hereby incorporated by reference to the extent not inconsistent with the disclosure herein.

We claim:

1. A method of treating cataracts, retinopathy, lens cell damage and retinal cell damage caused by diabetes comprising administering to a patient an effective amount of one or more compounds of the formula:

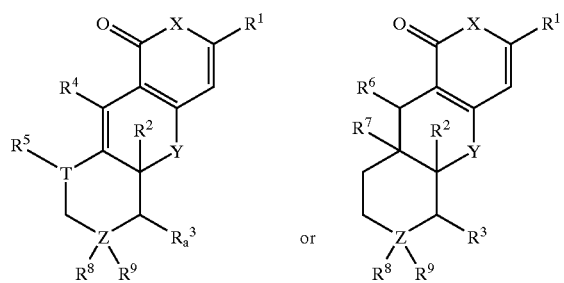

wherein:

T is independently CR, NR, NR, S or O;

X is independently O, NR, N or S;

Y is independently O, NR, N or S;

Z is independently C, N, S or O;

$R^1$, $R^3$, $R^4$ and $R^5$ are, independently, H, OH, alkyl, alkenyl, alkynyl, an aromatic ring system, amino, sulfhydryl, sulfonyl,

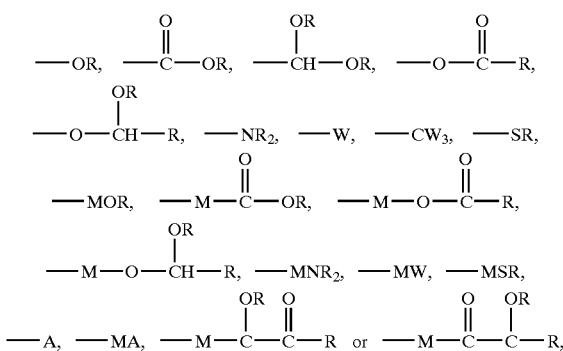

wherein R is independently H, OH, alkyl, alkenyl, alkynyl, an aromatic ring system, amino, sulfhydryl, or sulfonyl, M is a divalent alkyl, alkenyl or alkynyl, aromatic ring system, or sulfonyl, W is Cl, F, Br or OCl, and A is an aromatic ring system;

$R^2$, $R^8$ and $R^9$ are independently H, OH, alkyl, alkenyl, alkynyl, an aromatic ring system, amino, sulfhydryl, or sulfonyl; and $R^6$ is independently R, $NH_2$, OH, or OCOR where R is H, OH, alkyl, alkenyl, alkynyl, an aromatic ring system, amino, sulfhydryl, or sulfonyl;

$R^7$ is independently OH or H; or $R^6$ and $R^7$ taken together are O;

and pharmaceutically acceptable salts or esters of the foregoing, as well as optical isomers thereof.

2. The method of claim 1, wherein said patient is a dog and said compound is:

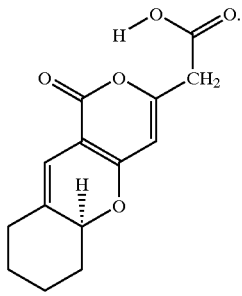

3. The method of claim 2, wherein the compound is administered orally.

4. The method of claim 2, wherein the compound is administered topically.

5. The method of claim 1, wherein said patient is a human and said compound is:

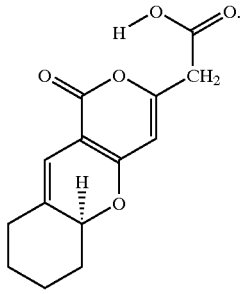

6. The method of claim 5, wherein the compound is administered orally.

7. The method of claim 5, wherein the compound is administered topically.

8. A method of reducing polyol accumulation in the eye, reducing galactitol formation from galactose in lens cells or reducing expression of aldose reductase in the retina caused by diabetes comprising administering to a patient an effective amount of one or more compounds of the formula:

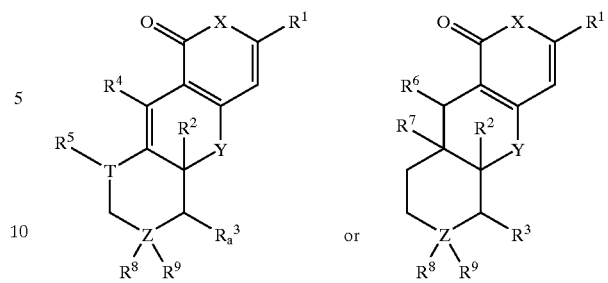

wherein:
T is independently CR, NR, N, S or O;
X is independently O, NR, N or S;
Y is independently O, NR, N or S;
Z is independently C, N, S or O;
$R^1$, $R^3$, $R^4$ and $R^5$ are, independently, H, OH, alkyl, alkenyl, alkynyl, an aromatic ring system, amino, sulfhydryl, sulfonyl,

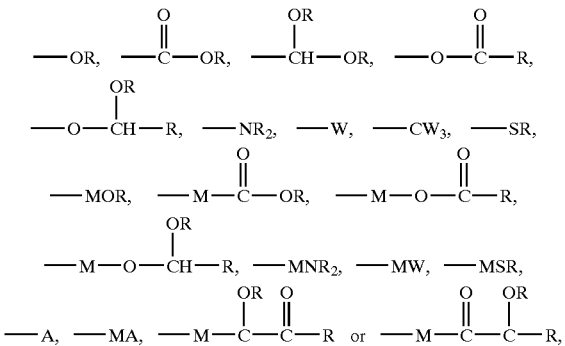

wherein R is independently H, OH, alkyl, alkenyl, alkynyl, an aromatic ring system, amino, sulfhydryl, or sulfonyl, M is a divalent alkyl, alkenyl or alkynyl, aromatic ring system, or sulfonyl, W is Cl, F, Br or OCl, and A is an aromatic ring system;
$R^2$, $R^8$ and $R^9$ are independently H, OH, alkyl, alkenyl, alkynyl, an aromatic ring system, amino, sulfhydryl, or sulfonyl; and
$R^6$ is independently R, $NH_2$, OH, or OCOR where R is H, OH, alkyl, alkenyl, alkynyl, an aromatic ring system, amino, sulfhydryl, or sulfonyl;
$R^7$ is independently OH or H; or
$R^6$ and $R^7$ taken together are O;
and pharmaceutically acceptable salts or esters of the foregoing, as well as optical isomers thereof.

* * * * *

UNITED STATES PATENT AND TRADEMARK OFFICE
CERTIFICATE OF CORRECTION

PATENT NO. : 6,916,824 B2
DATED : July 12, 2005
INVENTOR(S) : Hua et al.

Page 1 of 1

It is certified that error appears in the above-identified patent and that said Letters Patent is hereby corrected as shown below:

Column 17,
Lines 35 and 39, replace "Toirestat" with -- Tolrestat --.

Column 30,
Line 42, replace "diisopropylarnine" with -- diisopropylamine --.

Column 34,
Line 6, replace "140" with -- 0.140 --.

Column 38,
Line 11, replace "damage" with -- damage, --.
Line 25, in the first structure replace "$R_a^3$" with -- $R^3$ --.

Column 39,
Line 49, replace "retina" with -- retina, --.

Column 40,
Line 10, in the first structure replace "$R_a^3$" with -- $R^3$ --.

Signed and Sealed this

Eleventh Day of April, 2006

JON W. DUDAS
*Director of the United States Patent and Trademark Office*